(12) United States Patent
McCormick

(10) Patent No.: US 9,808,296 B2
(45) Date of Patent: Nov. 7, 2017

(54) HAMMERTOE IMPLANT AND INSTRUMENT

(71) Applicant: Wright Medical Technology, Inc., Memphis, TN (US)

(72) Inventor: Daniel F. McCormick, Memphis, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 47 days.

(21) Appl. No.: 14/403,746

(22) PCT Filed: Sep. 18, 2014

(86) PCT No.: PCT/US2014/056315
§ 371 (c)(1),
(2) Date: Nov. 25, 2014

(87) PCT Pub. No.: WO2016/043751
PCT Pub. Date: Mar. 24, 2016

(65) Prior Publication Data
US 2016/0081728 A1 Mar. 24, 2016

(51) Int. Cl.
*A61B 17/72* (2006.01)
*A61B 17/16* (2006.01)
(Continued)

(52) U.S. Cl.
CPC ...... *A61B 17/7291* (2013.01); *A61B 17/1604* (2013.01); *A61B 17/1617* (2013.01);
(Continued)

(58) Field of Classification Search
CPC ................................. A61B 17/7291
(Continued)

(56) References Cited

U.S. PATENT DOCUMENTS

| 321,389 A | 6/1885 | Schirmer |
| 346,148 A | 7/1886 | Durham |

(Continued)

FOREIGN PATENT DOCUMENTS

| CN | 1047025 A | 11/1990 |
| CN | 201085677 | 7/2008 |

(Continued)

OTHER PUBLICATIONS

International Searching Authority, Korean Intellectual Property Office, PCT International Search Report regarding corresponding PCT Application No. PCT/US2014/056315 dated May 22, 2015, pp. 1-6.

(Continued)

*Primary Examiner* — Nicholas Plionis
(74) *Attorney, Agent, or Firm* — Duane Morris LLP

(57) ABSTRACT

A bone implant comprising an elongate body having a first end and a second end coupled by a shaft is disclosed. The first portion is configured to couple to a first bone. The second portion comprises a first expandable section comprising at least one expandable feature. The first expandable section is configured to be received within a reverse countersink in a second bone in a collapsed state and to expand within the reverse countersink. The expandable feature couples to a bearing surface of the reverse countersink. A surgical tool comprising a shaft and at least one expandable cutting edge is disclosed. The shaft is sized and configured to be received within a canal formed in a bone. The expandable cutting edge is formed integrally with the shaft. The expandable cutting edge is configured to expand from a collapsed position to an expanded position for forming a reverse countersink.

22 Claims, 14 Drawing Sheets

(51) Int. Cl.
    *A61F 2/42*            (2006.01)
    *A61B 17/88*         (2006.01)

(52) U.S. Cl.
    CPC ...... *A61B 17/7266* (2013.01); *A61B 17/8872* (2013.01); *A61F 2/4225* (2013.01); *A61B 17/1682* (2013.01); *A61B 17/1686* (2013.01); *A61B 17/7283* (2013.01); *A61F 2002/423* (2013.01)

(58) Field of Classification Search
    USPC ....................................................... 606/62–64
    See application file for complete search history.

(56) References Cited

U.S. PATENT DOCUMENTS

| | | |
|---|---|---|
| 348,589 A | 9/1886 | Sloan |
| 373,074 A | 11/1887 | Jones |
| 430,236 A | 6/1890 | Rogers |
| 561,968 A | 6/1896 | Coulon |
| 736,121 A | 8/1903 | Lipscomb |
| 821,025 A | 5/1906 | Davies |
| 882,937 A | 3/1908 | Pegley |
| 1,966,835 A | 7/1934 | Stites |
| 2,140,749 A | 12/1938 | Kaplan |
| 2,361,107 A | 10/1944 | Johnson |
| 2,451,747 A | 10/1948 | Kindt |
| 2,490,364 A | 12/1949 | Livingston |
| 2,600,517 A | 6/1952 | Rushing |
| 2,697,370 A | 12/1954 | Brooks |
| 2,832,245 A | 4/1958 | Burrows |
| 2,895,368 A | 7/1959 | Place |
| 3,462,765 A | 8/1969 | Swanson |
| 3,466,669 A | 9/1969 | Flatt |
| 3,593,342 A | 7/1971 | Niebauer et al. |
| 3,681,786 A | 8/1972 | Lynch |
| 3,739,403 A | 6/1973 | Nicolle |
| 3,759,257 A | 9/1973 | Fischer et al. |
| 3,760,802 A | 9/1973 | Fischer et al. |
| 3,779,239 A | 12/1973 | Fischer et al. |
| 3,824,631 A | 7/1974 | Burstein et al. |
| D243,716 S | 3/1977 | Treace et al. |
| 4,047,524 A | 9/1977 | Hall |
| 4,096,896 A | 6/1978 | Engel |
| 4,156,296 A | 5/1979 | Johnson et al. |
| 4,170,990 A | 10/1979 | Baumgart et al. |
| 4,175,555 A | 11/1979 | Herbert |
| 4,198,713 A | 4/1980 | Swanson |
| 4,204,284 A | 5/1980 | Koeneman |
| 4,213,208 A | 7/1980 | Marne |
| 4,237,875 A | 12/1980 | Termanini |
| 4,262,665 A | 4/1981 | Roalstad et al. |
| 4,263,903 A | 4/1981 | Griggs |
| 4,275,717 A | 6/1981 | Bolesky |
| 4,276,660 A | 7/1981 | Laure |
| 4,278,091 A | 7/1981 | Borzone |
| 4,304,011 A | 12/1981 | Whelan, III |
| 4,321,002 A | 3/1982 | Froehlich |
| 4,364,382 A | 12/1982 | Mennen |
| 4,367,562 A | 1/1983 | Gauthier |
| 4,404,874 A | 9/1983 | Lieser |
| 4,434,796 A | 3/1984 | Karapetian et al. |
| 4,454,875 A | 6/1984 | Pratt et al. |
| 4,485,816 A | 12/1984 | Krumme |
| D277,509 S | 2/1985 | Lawrence et al. |
| D277,784 S | 2/1985 | Sgariato et al. |
| 4,516,569 A | 5/1985 | Evans et al. |
| 4,570,623 A | 2/1986 | Ellison et al. |
| 4,590,928 A | 5/1986 | Hunt et al. |
| D284,099 S | 6/1986 | Laporta et al. |
| 4,634,382 A | 1/1987 | Kusano et al. |
| 4,642,122 A | 2/1987 | Steffee |
| 4,655,661 A | 4/1987 | Brandt |
| D291,731 S | 9/1987 | Aikins |
| 4,723,540 A | 2/1988 | Gilmer, Jr. |
| 4,723,541 A | 2/1988 | Reese |
| 4,731,087 A | 3/1988 | Sculco et al. |
| 4,756,711 A | 7/1988 | Mai et al. |
| 4,759,768 A | 7/1988 | Hermann et al. |
| 4,790,304 A | 12/1988 | Rosenberg |
| 4,865,606 A | 9/1989 | Rehder |
| 4,908,031 A | 3/1990 | Frisch |
| 4,915,092 A | 4/1990 | Firica et al. |
| 4,932,974 A | 6/1990 | Pappas et al. |
| 4,940,467 A | 7/1990 | Tronzo |
| 4,955,916 A | 9/1990 | Carignan et al. |
| 4,963,144 A | 10/1990 | Huene |
| 4,969,909 A | 11/1990 | Barouk |
| 5,002,563 A | 3/1991 | Pyka et al. |
| 5,007,932 A | 4/1991 | Bekki et al. |
| 5,011,497 A | 4/1991 | Persson et al. |
| 5,019,079 A | 5/1991 | Ross |
| 5,029,753 A | 7/1991 | Hipon et al. |
| 5,037,440 A | 8/1991 | Koenig |
| 5,046,513 A | 9/1991 | Gatturna et al. |
| 5,047,059 A | 9/1991 | Saffar |
| 5,053,038 A | 10/1991 | Sheehan |
| 5,059,193 A | 10/1991 | Kuslich |
| 5,062,851 A | 11/1991 | Branemark |
| 5,089,009 A | 2/1992 | Green |
| 5,092,896 A | 3/1992 | Meuli et al. |
| 5,108,395 A | 4/1992 | Laurain |
| 5,133,761 A | 7/1992 | Krouskop |
| 5,147,363 A | 9/1992 | Harle |
| 5,171,252 A | 12/1992 | Friedland |
| 5,179,915 A | 1/1993 | Cohen et al. |
| 5,190,546 A | 3/1993 | Jervis |
| 5,199,839 A | 4/1993 | DeHaitre |
| 5,207,712 A | 5/1993 | Cohen |
| 5,209,756 A | 5/1993 | Seedhom et al. |
| 5,213,347 A | 5/1993 | Rulon et al. |
| 5,222,975 A | 6/1993 | Crainich |
| 5,246,443 A | 9/1993 | Mai |
| 5,281,225 A | 1/1994 | Vicenzi |
| 5,304,204 A | 4/1994 | Bregen |
| 5,324,307 A | 6/1994 | Jarrett et al. |
| 5,326,364 A | 7/1994 | Clift, Jr. et al. |
| 5,326,366 A | 7/1994 | Pascarella et al. |
| 5,330,476 A | 7/1994 | Hiot et al. |
| 5,342,396 A | 8/1994 | Cook |
| 5,352,229 A | 10/1994 | Goble et al. |
| 5,354,301 A | 10/1994 | Castellano |
| 5,358,405 A | 10/1994 | Imai |
| 5,360,450 A | 11/1994 | Giannini |
| 5,366,479 A | 11/1994 | McGarry et al. |
| 5,380,334 A | 1/1995 | Torrie et al. |
| 5,395,372 A | 3/1995 | Holt et al. |
| 5,405,400 A | 4/1995 | Linscheid et al. |
| 5,405,401 A | 4/1995 | Lippincott, III et al. |
| 5,417,692 A | 5/1995 | Goble et al. |
| 5,425,776 A | 6/1995 | Cohen |
| 5,425,777 A | 6/1995 | Sarkisian et al. |
| 5,437,674 A | 8/1995 | Worcel et al. |
| 5,449,359 A | 9/1995 | Groiso |
| 5,454,814 A | 10/1995 | Comte |
| 5,458,648 A | 10/1995 | Berman et al. |
| 5,470,230 A | 11/1995 | Daftary et al. |
| 5,474,557 A | 12/1995 | Mai |
| 5,480,447 A | 1/1996 | Skiba |
| 5,484,443 A | 1/1996 | Pascarella et al. |
| 5,498,265 A | 3/1996 | Asnis et al. |
| 5,507,822 A | 4/1996 | Bouchon et al. |
| 5,516,248 A | 5/1996 | DeHaitre |
| 5,522,903 A | 6/1996 | Sokolow et al. |
| 5,529,075 A | 6/1996 | Clark |
| 5,536,127 A | 7/1996 | Pennig |
| 5,549,681 A | 8/1996 | Segmüller et al. |
| 5,551,871 A | 9/1996 | Besselink et al. |
| 5,554,157 A | 9/1996 | Errico et al. |
| 5,578,034 A | 11/1996 | Estes |
| 5,591,165 A | 1/1997 | Jackson |
| 5,595,563 A | 1/1997 | Moisdon |
| 5,601,558 A | 2/1997 | Torrie et al. |
| D378,409 S | 3/1997 | Michelson |

(56) References Cited

U.S. PATENT DOCUMENTS

| | | |
|---|---|---|
| 5,634,925 A | 6/1997 | Urbanski |
| 5,643,264 A | 7/1997 | Sherman et al. |
| 5,645,599 A | 7/1997 | Samani |
| 5,660,188 A | 8/1997 | Groiso |
| 5,669,913 A | 9/1997 | Zobel |
| 5,674,297 A | 10/1997 | Lane et al. |
| 5,683,466 A | 11/1997 | Vitale |
| 5,690,629 A | 11/1997 | Asher et al. |
| 5,702,472 A | 12/1997 | Huebner |
| 5,707,395 A | 1/1998 | Li |
| 5,713,903 A | 2/1998 | Sander et al. |
| 5,713,904 A | 2/1998 | Errico et al. |
| 5,720,753 A | 2/1998 | Sander et al. |
| 5,725,585 A | 3/1998 | Zobel |
| 5,728,127 A | 3/1998 | Asher et al. |
| 5,733,307 A | 3/1998 | Dinsdale |
| 5,741,256 A | 4/1998 | Bresina |
| 5,749,916 A | 5/1998 | Richelsoph |
| 5,769,852 A | 6/1998 | Brånemark |
| 5,776,202 A | 7/1998 | Copf et al. |
| 5,779,707 A | 7/1998 | Bertholet et al. |
| 5,782,927 A | 7/1998 | Klawitter et al. |
| 5,785,713 A | 7/1998 | Jobe |
| 5,840,078 A | 11/1998 | Yerys |
| 5,853,414 A | 12/1998 | Groiso |
| 5,876,434 A | 3/1999 | Flomenblit et al. |
| 5,882,444 A | 3/1999 | Flomenblit et al. |
| 5,893,850 A | 4/1999 | Cachia |
| 5,919,193 A | 7/1999 | Slavitt |
| 5,928,236 A | 7/1999 | Augagneur et al. |
| 5,941,890 A | 8/1999 | Voegele et al. |
| 5,951,288 A | 9/1999 | Sawa |
| 5,958,159 A | 9/1999 | Prandi |
| 5,980,524 A | 11/1999 | Justin et al. |
| 5,984,970 A | 11/1999 | Bramlet |
| 5,984,971 A | 11/1999 | Faccioli et al. |
| 6,011,497 A | 1/2000 | Tsang et al. |
| 6,017,366 A | 1/2000 | Berman |
| 6,030,162 A | 2/2000 | Huebner |
| 6,045,573 A | 4/2000 | Wenstrom, Jr. et al. |
| 6,048,151 A | 4/2000 | Kwee |
| 6,048,343 A | 4/2000 | Mathis et al. |
| 6,083,242 A | 7/2000 | Cook |
| 6,099,571 A | 8/2000 | Knapp |
| 6,102,642 A | 8/2000 | Kawashita et al. |
| 6,146,387 A | 11/2000 | Trott et al. |
| 6,187,009 B1 | 2/2001 | Herzog et al. |
| 6,193,757 B1 | 2/2001 | Foley et al. |
| 6,197,037 B1 | 3/2001 | Hair |
| 6,200,321 B1 | 3/2001 | Orbay et al. |
| 6,200,330 B1 | 3/2001 | Benderev et al. |
| 6,200,345 B1 | 3/2001 | Morgan |
| 6,224,600 B1 | 5/2001 | Protogirou |
| 6,248,109 B1 | 6/2001 | Stoffella |
| 6,299,613 B1 | 10/2001 | Ogilvie et al. |
| 6,305,053 B1 | 10/2001 | Galbreath |
| 6,306,140 B1 | 10/2001 | Siddiqui |
| 6,319,284 B1 | 11/2001 | Rushdy et al. |
| 6,332,885 B1 | 12/2001 | Martella |
| 6,336,928 B1 | 1/2002 | Guerin et al. |
| 6,352,560 B1 | 3/2002 | Poeschmann et al. |
| 6,383,223 B1 | 5/2002 | Baehler et al. |
| 6,386,877 B1 | 5/2002 | Sutter |
| 6,406,234 B2 | 6/2002 | Frigg |
| 6,413,260 B1 | 7/2002 | Berrevoets et al. |
| 6,419,706 B1 | 7/2002 | Graf |
| 6,423,097 B2 | 7/2002 | Rauscher |
| 6,428,634 B1 | 8/2002 | Besselink et al. |
| 6,436,099 B1 | 8/2002 | Drewry et al. |
| 6,451,057 B1 | 9/2002 | Chen et al. |
| 6,454,808 B1 | 9/2002 | Masada |
| 6,458,134 B1 | 10/2002 | Songer et al. |
| 6,475,242 B1 | 11/2002 | Bramlet |
| 6,508,841 B2 | 1/2003 | Martin et al. |
| 6,517,543 B1 | 2/2003 | Berrevoets et al. |
| 6,533,788 B1 | 3/2003 | Orbay |
| 6,551,321 B1 | 4/2003 | Burkinshaw |
| 6,551,343 B1 | 4/2003 | Törmälä et al. |
| 6,575,973 B1 | 6/2003 | Shekalim |
| 6,575,976 B2 | 6/2003 | Grafton |
| 6,582,453 B1 | 6/2003 | Tran et al. |
| 6,648,890 B2 | 11/2003 | Culbert et al. |
| 6,679,668 B2 | 1/2004 | Martin et al. |
| 6,682,565 B1 | 1/2004 | Krishnan |
| 6,685,706 B2 | 2/2004 | Padget et al. |
| 6,699,247 B2 | 3/2004 | Zucherman et al. |
| 6,699,292 B2 | 3/2004 | Ogilvie et al. |
| 6,706,045 B2 | 3/2004 | Lin et al. |
| 6,767,350 B1 | 7/2004 | Lob |
| 6,773,437 B2 | 8/2004 | Ogilvie et al. |
| 6,811,568 B2 | 11/2004 | Minamikawa |
| 6,869,449 B2 | 3/2005 | Ball et al. |
| 6,875,235 B2 | 4/2005 | Ferree |
| 7,037,309 B2 | 5/2006 | Weil et al. |
| 7,037,324 B2 | 5/2006 | Martinek |
| 7,037,342 B2 | 5/2006 | Nilsson et al. |
| 7,041,106 B1 | 5/2006 | Carver et al. |
| 7,044,953 B2 | 5/2006 | Capanni |
| 7,112,214 B2 | 9/2006 | Peterson et al. |
| 7,182,787 B2 | 2/2007 | Hassler et al. |
| 7,192,445 B2 | 3/2007 | Ellingsen et al. |
| 7,207,994 B2 | 4/2007 | Vlahos et al. |
| 7,240,677 B2 | 7/2007 | Fox |
| 7,261,716 B2 | 8/2007 | Strobel |
| 7,291,175 B1 | 11/2007 | Gordon |
| 7,569,061 B2 | 8/2009 | Colleran |
| 7,585,316 B2 | 9/2009 | Trieu |
| 7,588,603 B2 | 9/2009 | Leonard |
| 7,695,471 B2 | 4/2010 | Cheung et al. |
| 7,708,759 B2 | 5/2010 | Lubbers et al. |
| 7,727,235 B2 | 6/2010 | Contiliano et al. |
| 7,780,701 B1 | 8/2010 | Meridew et al. |
| 7,780,737 B2 | 8/2010 | Bonnard et al. |
| 7,785,357 B2 | 8/2010 | Guan et al. |
| 7,837,738 B2 | 11/2010 | Reigstad et al. |
| 7,842,091 B2 | 11/2010 | Johnstone et al. |
| 7,887,589 B2 | 2/2011 | Glenn et al. |
| 7,909,880 B1 | 3/2011 | Grant |
| 7,918,879 B2 | 4/2011 | Yeung et al. |
| 7,959,681 B2 | 6/2011 | Lavi |
| 7,963,995 B2 | 6/2011 | Richelsoph |
| 7,976,565 B1 | 7/2011 | Meridew |
| 7,985,246 B2 | 7/2011 | Trieu |
| 8,002,811 B2 | 8/2011 | Corradi et al. |
| 8,057,524 B2 | 11/2011 | Meridew |
| 8,100,983 B2 | 1/2012 | Schulte |
| 8,118,839 B2 | 2/2012 | Taylor |
| 8,118,849 B2 | 2/2012 | Wahl et al. |
| 8,197,509 B2 | 6/2012 | Contiliano et al. |
| 8,262,712 B2 | 9/2012 | Coilard-Lavirotte et al. |
| 8,267,939 B2 | 9/2012 | Cipoletti et al. |
| 8,337,537 B2 | 12/2012 | Pelo et al. |
| 8,394,097 B2 | 3/2013 | Peyrot et al. |
| 8,394,132 B2 | 3/2013 | Lewis et al. |
| 8,414,583 B2 | 4/2013 | Prandi et al. |
| 8,465,525 B2 | 6/2013 | Hawkins et al. |
| 8,475,456 B2 | 7/2013 | Augoyard et al. |
| 8,523,944 B2 | 9/2013 | Jimenez et al. |
| 8,591,545 B2 | 11/2013 | Lunn et al. |
| 8,608,785 B2 | 12/2013 | Reed et al. |
| 8,616,091 B2 | 12/2013 | Anderson |
| 8,636,457 B2 | 1/2014 | Connors |
| 8,641,769 B2 | 2/2014 | Malandain |
| 8,647,390 B2 | 2/2014 | Bellemere et al. |
| 8,764,842 B2 | 7/2014 | Graham |
| 8,840,677 B2 | 9/2014 | Kale et al. |
| 8,888,779 B2 | 11/2014 | Senn |
| D720,072 S | 12/2014 | Cheney et al. |
| 8,906,060 B2 | 12/2014 | Hart |
| 8,986,386 B2 | 3/2015 | Oglaza et al. |
| 8,998,999 B2 | 4/2015 | Lewis et al. |
| 9,044,287 B2 | 6/2015 | Reed et al. |
| 9,056,014 B2 | 6/2015 | McCormick et al. |
| 9,125,704 B2 | 9/2015 | Reed et al. |

(56) References Cited

U.S. PATENT DOCUMENTS

| | | |
|---|---|---|
| 9,138,274 B1 | 9/2015 | Biesinger et al. |
| 9,149,268 B2 | 10/2015 | Graul et al. |
| 2001/0025199 A1 | 9/2001 | Rauscher |
| 2001/0028836 A1 | 10/2001 | Kohori |
| 2001/0049529 A1 | 12/2001 | Cachia et al. |
| 2002/0019636 A1 | 2/2002 | Ogilvie et al. |
| 2002/0022887 A1 | 2/2002 | Huene |
| 2002/0026194 A1 | 2/2002 | Morrison et al. |
| 2002/0055785 A1 | 5/2002 | Harris |
| 2002/0065561 A1 | 5/2002 | Ogilvie et al. |
| 2002/0068939 A1 | 6/2002 | Levy et al. |
| 2002/0072803 A1 | 6/2002 | Saunders et al. |
| 2002/0082705 A1 | 6/2002 | Bouman et al. |
| 2002/0111690 A1 | 8/2002 | Hyde |
| 2002/0128713 A1 | 9/2002 | Ferree |
| 2002/0165544 A1 | 11/2002 | Perren et al. |
| 2002/0183846 A1 | 12/2002 | Kuslich et al. |
| 2003/0032961 A1 | 2/2003 | Pelo et al. |
| 2003/0040805 A1 | 2/2003 | Minamikawa |
| 2003/0069645 A1 | 4/2003 | Ball et al. |
| 2003/0130660 A1 | 7/2003 | Levy et al. |
| 2003/0191422 A1 | 10/2003 | Sossong |
| 2003/0233095 A1 | 12/2003 | Urbanski et al. |
| 2004/0010315 A1 | 1/2004 | Song |
| 2004/0093081 A1 | 5/2004 | Nilsson et al. |
| 2004/0097941 A1 | 5/2004 | Weiner et al. |
| 2004/0102853 A1 | 5/2004 | Boumann et al. |
| 2004/0111117 A1 | 6/2004 | Colleran et al. |
| 2004/0133204 A1 | 7/2004 | Davies |
| 2004/0138756 A1 | 7/2004 | Reeder |
| 2004/0220574 A1 | 11/2004 | Pelo et al. |
| 2004/0220678 A1 | 11/2004 | Chow et al. |
| 2004/0230193 A1 | 11/2004 | Cheung et al. |
| 2004/0230194 A1 | 11/2004 | Urbanski et al. |
| 2004/0230313 A1 | 11/2004 | Saunders |
| 2004/0249461 A1 | 12/2004 | Ferree |
| 2005/0113836 A1 | 5/2005 | Lozier et al. |
| 2005/0119757 A1 | 6/2005 | Hassler et al. |
| 2005/0123672 A1 | 6/2005 | Justin et al. |
| 2005/0124443 A1 | 6/2005 | Summers |
| 2005/0149031 A1 | 7/2005 | Ciccone et al. |
| 2005/0177158 A1 | 8/2005 | Doubler et al. |
| 2005/0187636 A1 | 8/2005 | Graham |
| 2005/0251265 A1 | 11/2005 | Calandruccio et al. |
| 2005/0261768 A1 | 11/2005 | Trieu |
| 2005/0283159 A1 | 12/2005 | Amara |
| 2006/0052725 A1 | 3/2006 | Santilli |
| 2006/0052878 A1 | 3/2006 | Schmieding |
| 2006/0074421 A1 | 4/2006 | Bickley et al. |
| 2006/0074488 A1 | 4/2006 | Abdou |
| 2006/0074492 A1 | 4/2006 | Frey |
| 2006/0084998 A1 | 4/2006 | Levy et al. |
| 2006/0100715 A1 | 5/2006 | De Villiers |
| 2006/0129153 A1 | 6/2006 | Klaue et al. |
| 2006/0149258 A1 | 7/2006 | Sousa |
| 2006/0173462 A1 | 8/2006 | Kay et al. |
| 2006/0200151 A1 | 9/2006 | Ducharme et al. |
| 2006/0229617 A1 | 10/2006 | Meller et al. |
| 2006/0247787 A1 | 11/2006 | Rydell et al. |
| 2007/0038303 A1 | 2/2007 | Myerson et al. |
| 2007/0078518 A1 | 4/2007 | Lavi |
| 2007/0106283 A1 | 5/2007 | Garcia et al. |
| 2007/0123873 A1 | 5/2007 | Czartoski et al. |
| 2007/0123993 A1 | 5/2007 | Hassler et al. |
| 2007/0142920 A1 | 6/2007 | Niemi |
| 2007/0177959 A1 | 8/2007 | Chopp et al. |
| 2007/0185583 A1 | 8/2007 | Branemark |
| 2007/0185584 A1 | 8/2007 | Kaufmann et al. |
| 2007/0198018 A1 | 8/2007 | Biedermann et al. |
| 2007/0213831 A1 | 9/2007 | de Cubber |
| 2007/0239158 A1 | 10/2007 | Trieu et al. |
| 2007/0293866 A1 | 12/2007 | Stoeckel et al. |
| 2008/0039949 A1 | 2/2008 | Meesenburg et al. |
| 2008/0051912 A1 | 2/2008 | Hollawell |
| 2008/0086139 A1 | 4/2008 | Bourke et al. |
| 2008/0132894 A1 | 6/2008 | Coilard-Lavirotte et al. |
| 2008/0132958 A1 | 6/2008 | Pech et al. |
| 2008/0154385 A1 | 6/2008 | Trail et al. |
| 2008/0161919 A1 | 7/2008 | Melkent |
| 2008/0177262 A1 | 7/2008 | Augoyard et al. |
| 2008/0177291 A1 | 7/2008 | Jensen et al. |
| 2008/0177334 A1 | 7/2008 | Stinnette |
| 2008/0195215 A1 | 8/2008 | Morton |
| 2008/0195219 A1 | 8/2008 | Wiley et al. |
| 2008/0221574 A1 | 9/2008 | Cavallazzi |
| 2008/0221697 A1 | 9/2008 | Graser |
| 2008/0221698 A1 | 9/2008 | Berger |
| 2008/0255618 A1 | 10/2008 | Fisher et al. |
| 2008/0269908 A1 | 10/2008 | Warburton |
| 2008/0294204 A1 | 11/2008 | Chirico et al. |
| 2009/0005782 A1 | 1/2009 | Chirico et al. |
| 2009/0012564 A1 | 1/2009 | Chirico et al. |
| 2009/0036893 A1 | 2/2009 | Kartalian et al. |
| 2009/0105767 A1 | 4/2009 | Reiley |
| 2009/0149891 A1 | 6/2009 | Lee et al. |
| 2009/0163918 A1 | 6/2009 | Levy et al. |
| 2009/0171359 A1* | 7/2009 | Sterrett ............... A61B 1/317 606/80 |
| 2009/0187219 A1 | 7/2009 | Pachtman et al. |
| 2009/0204158 A1 | 8/2009 | Sweeney |
| 2009/0210016 A1 | 8/2009 | Champagne et al. |
| 2009/0216282 A1 | 8/2009 | Blake et al. |
| 2009/0254189 A1 | 10/2009 | Scheker |
| 2009/0254190 A1 | 10/2009 | Gannoe et al. |
| 2009/0259316 A1 | 10/2009 | Ginn et al. |
| 2010/0010637 A1 | 1/2010 | Pequignot |
| 2010/0016982 A1 | 1/2010 | Solomons |
| 2010/0023012 A1 | 1/2010 | Voor |
| 2010/0030221 A1 | 2/2010 | Christian et al. |
| 2010/0049244 A1 | 2/2010 | Cohen et al. |
| 2010/0057214 A1 | 3/2010 | Graham et al. |
| 2010/0061825 A1 | 3/2010 | Liu et al. |
| 2010/0069913 A1* | 3/2010 | Chirico ............ A61B 17/1617 606/94 |
| 2010/0069970 A1 | 3/2010 | Lewis et al. |
| 2010/0121390 A1 | 5/2010 | Kleinman |
| 2010/0125274 A1 | 5/2010 | Greenhalgh et al. |
| 2010/0131014 A1 | 5/2010 | Peyrot et al. |
| 2010/0131072 A1 | 5/2010 | Schulte |
| 2010/0161068 A1 | 6/2010 | Lindner et al. |
| 2010/0185295 A1 | 7/2010 | Emmanuel |
| 2010/0217325 A1 | 8/2010 | Hochschuler et al. |
| 2010/0249942 A1 | 9/2010 | Goswami et al. |
| 2010/0256639 A1 | 10/2010 | Tyber et al. |
| 2010/0256770 A1 | 10/2010 | Hakansson et al. |
| 2010/0262254 A1 | 10/2010 | Lawrence et al. |
| 2010/0274256 A1* | 10/2010 | Ritchey ................ A61B 5/05 606/96 |
| 2010/0274293 A1 | 10/2010 | Terrill et al. |
| 2010/0286692 A1 | 11/2010 | Greenhalgh et al. |
| 2010/0292799 A1 | 11/2010 | Hansell et al. |
| 2010/0324556 A1 | 12/2010 | Tyber et al. |
| 2010/0331893 A1 | 12/2010 | Geist et al. |
| 2011/0004255 A1 | 1/2011 | Weiner et al. |
| 2011/0004317 A1 | 1/2011 | Hacking et al. |
| 2011/0066190 A1 | 3/2011 | Schaller et al. |
| 2011/0082507 A1 | 4/2011 | Klaue |
| 2011/0082508 A1 | 4/2011 | Reed |
| 2011/0093017 A1 | 4/2011 | Prasad et al. |
| 2011/0093075 A1 | 4/2011 | Duplessis et al. |
| 2011/0093085 A1 | 4/2011 | Morton |
| 2011/0118739 A1 | 5/2011 | Tyber et al. |
| 2011/0144644 A1 | 6/2011 | Prandi et al. |
| 2011/0144766 A1 | 6/2011 | Kale et al. |
| 2011/0160870 A1* | 6/2011 | Baumgartner ............ A61F 2/28 623/23.61 |
| 2011/0208252 A1 | 8/2011 | Erhart |
| 2011/0257652 A1 | 10/2011 | Roman |
| 2011/0301652 A1 | 12/2011 | Reed et al. |
| 2011/0301653 A1 | 12/2011 | Reed et al. |
| 2011/0306975 A1 | 12/2011 | Kaikkonen et al. |
| 2011/0319946 A1 | 12/2011 | Levy et al. |
| 2012/0016428 A1 | 1/2012 | White et al. |
| 2012/0065692 A1 | 3/2012 | Champagne et al. |

(56) References Cited

U.S. PATENT DOCUMENTS

| | | |
|---|---|---|
| 2012/0065738 A1 | 3/2012 | Schulman |
| 2012/0089197 A1 | 4/2012 | Anderson |
| 2012/0136448 A1 | 5/2012 | Seifert et al. |
| 2012/0209337 A1 | 8/2012 | Weinstein |
| 2012/0259419 A1 | 10/2012 | Brown et al. |
| 2012/0271362 A1 | 10/2012 | Martineau et al. |
| 2012/0323241 A1 | 12/2012 | McClellan et al. |
| 2013/0030475 A1 | 1/2013 | Weiner et al. |
| 2013/0053975 A1 | 2/2013 | Reed et al. |
| 2013/0060295 A1 | 3/2013 | Reed et al. |
| 2013/0066383 A1 | 3/2013 | Anderson et al. |
| 2013/0066435 A1 | 3/2013 | Averous et al. |
| 2013/0079776 A1 | 3/2013 | Zwirkoski et al. |
| 2013/0090655 A1 | 4/2013 | Tontz |
| 2013/0096634 A1 | 4/2013 | Suh |
| 2013/0123862 A1 | 5/2013 | Anderson et al. |
| 2013/0131822 A1* | 5/2013 | Lewis .................. A61F 2/4606 623/21.19 |
| 2013/0150965 A1 | 6/2013 | Taylor et al. |
| 2013/0190761 A1 | 7/2013 | Prandi et al. |
| 2013/0211451 A1 | 8/2013 | Wales et al. |
| 2013/0226191 A1 | 8/2013 | Thoren et al. |
| 2013/0253597 A1 | 9/2013 | Augoyard et al. |
| 2013/0274814 A1 | 10/2013 | Weiner et al. |
| 2013/0317559 A1 | 11/2013 | Leavitt et al. |
| 2013/0325138 A1 | 12/2013 | Graham |
| 2014/0018930 A1 | 1/2014 | Oster |
| 2014/0025125 A1 | 1/2014 | Sack et al. |
| 2014/0052196 A1 | 2/2014 | McGinley et al. |
| 2014/0107713 A1 | 4/2014 | Pech et al. |
| 2014/0135768 A1 | 5/2014 | Roman |
| 2014/0142715 A1 | 5/2014 | McCormick |
| 2014/0180428 A1 | 6/2014 | McCormick |
| 2014/0188179 A1 | 7/2014 | McCormick |
| 2014/0188237 A1 | 7/2014 | McCormick et al. |
| 2014/0188239 A1 | 7/2014 | Cummings |
| 2014/0257289 A1 | 9/2014 | Kecman et al. |
| 2014/0276825 A1 | 9/2014 | Brown et al. |
| 2014/0277185 A1 | 9/2014 | Boileau et al. |
| 2014/0277186 A1 | 9/2014 | Granberry et al. |
| 2015/0012098 A1 | 1/2015 | Eastlack et al. |
| 2015/0018954 A1 | 1/2015 | Loebl et al. |
| 2015/0073413 A1 | 3/2015 | Palmer et al. |
| 2015/0088136 A1 | 3/2015 | Vitek et al. |
| 2015/0088266 A1 | 3/2015 | Sander et al. |
| 2015/0094778 A1 | 4/2015 | McCormick et al. |
| 2015/0112342 A1 | 4/2015 | Penzimer et al. |
| 2015/0141994 A1 | 5/2015 | Cheney et al. |
| 2015/0142066 A1 | 5/2015 | Shemwell et al. |
| 2015/0164563 A1 | 6/2015 | Lewis et al. |
| 2015/0223849 A1 | 8/2015 | McCormick et al. |
| 2015/0342655 A1 | 12/2015 | Reed et al. |

FOREIGN PATENT DOCUMENTS

| | | |
|---|---|---|
| EP | 0127994 | 12/1984 |
| EP | 0340159 A1 | 11/1989 |
| EP | 0409364 A2 | 1/1991 |
| EP | 0545830 | 6/1993 |
| EP | 0551846 A1 | 7/1993 |
| EP | 0611557 A3 | 8/1994 |
| EP | 0738502 A2 | 10/1996 |
| EP | 880950 A1 | 12/1998 |
| EP | 1300122 | 4/2003 |
| EP | 1825826 A1 | 8/2007 |
| EP | 1870050 A2 | 12/2007 |
| EP | 1708653 B1 | 9/2009 |
| EP | 1923012 B1 | 6/2010 |
| EP | 1868536 B1 | 11/2010 |
| EP | 2275055 B1 | 5/2012 |
| EP | 2221025 B1 | 12/2012 |
| EP | 2221026 B1 | 3/2013 |
| EP | 2564799 A1 | 3/2013 |
| EP | 2774556 A1 | 9/2014 |
| FR | 736058 | 11/1932 |
| FR | 1036978 | 9/1953 |
| FR | 2603794 | 3/1988 |
| FR | 2605878 A1 | 5/1988 |
| FR | 2628312 | 9/1989 |
| FR | 2645735 A1 | 10/1990 |
| FR | 2651119 A1 | 3/1991 |
| FR | 2663838 A1 | 1/1993 |
| FR | 2694696 | 2/1994 |
| FR | 2725126 | 4/1996 |
| FR | 2743490 | 7/1997 |
| FR | 2754702 | 4/1998 |
| FR | 2783702 A1 | 3/2000 |
| FR | 2787313 A1 | 6/2000 |
| FR | 2794019 A1 | 12/2000 |
| FR | 2801189 A1 | 5/2001 |
| FR | 2846545 A1 | 5/2004 |
| FR | 2728779 A1 | 7/2005 |
| FR | 2884406 | 10/2006 |
| FR | 2927529 A1 | 8/2009 |
| FR | 2935601 A1 | 3/2010 |
| GB | 140983 | 4/1920 |
| GB | 2119655 A | 11/1983 |
| GB | 2227540 A | 8/1990 |
| GB | 2336415 A | 10/1999 |
| GB | 2430625 A | 4/2007 |
| JP | S53-128181 A | 11/1978 |
| JP | 60145133 | 7/1985 |
| JP | H07-500520 A | 1/1995 |
| JP | 07303662 | 11/1995 |
| JP | 2004535249 | 11/2004 |
| JP | 2007530194 | 11/2007 |
| JP | 2008-188411 A | 8/2008 |
| JP | 2009-160399 A | 7/2009 |
| JP | 2010-046481 A | 3/2010 |
| JP | 2011-502584 A | 1/2011 |
| JP | 2011-525229 A | 9/2011 |
| SU | 1152582 | 4/1985 |
| WO | WO 92/17122 | 10/1992 |
| WO | WO 96/41596 A1 | 12/1996 |
| WO | WO 98/17189 | 4/1998 |
| WO | WO 98/47449 A1 | 10/1998 |
| WO | WO 99/21515 A1 | 5/1999 |
| WO | WO 01/80751 A1 | 11/2001 |
| WO | WO 02/34107 A2 | 5/2002 |
| WO | WO 2005/063149 | 7/2005 |
| WO | WO 2005/094706 A1 | 10/2005 |
| WO | WO 2005/104961 | 11/2005 |
| WO | WO 2006/109004 A1 | 10/2006 |
| WO | WO 2006103598 A1 | 10/2006 |
| WO | WO 2007/048038 | 4/2007 |
| WO | WO 2007/135322 A1 | 11/2007 |
| WO | WO 2009/155577 A2 | 12/2009 |
| WO | WO 2013/096746 A1 | 6/2013 |
| WO | WO 2013/131974 A1 | 9/2013 |
| WO | WO 2014/165123 A1 | 10/2014 |

OTHER PUBLICATIONS

International Searching Authority, Korean Intellectual Property Office, PCT Written Opinion of the International Searching Authority regarding corresponding PCT Application No. PCT/US2014/056315 dated May 22, 2015, pp. 1-9.

Bensmann, et al., "Nickel-titanium Osteosynthesis Clips," Reprint from Medical Focus, 1983.

Dai, K.R., et al., "Treatment of Intra-Articular Fractures with Shape Memory Compression Staples," Injury, (1993) 24, (IO), 651-655.

Kuo, M.D., et al., "The Use of Nickel-Titanium Alloy in Orthopedic Surgery in China," Orthopedics, Jan. 1989, vol. 12/No. 1.

Ricart, "The Use of a Memory Shape Staple in Cervical Anterior Fusion," Proceedings of the Second International Conference on Shape Memory and Superelastic Technologies, Asilomar Conference Center, Pacific Grove, CA, USA, Mar. 2-6, 1997.

Ricart, "The Use of a Memory-Shaple Staple in Cervical Anterior Fusion," in Shape Memory Implants, Springer-Verlag Berlin Heidelberg, 2000.

(56) References Cited

OTHER PUBLICATIONS

Tang, Dai, Chen ,"Application of a Ni-Ti Staple in the Metatarsal Osteotomy," Bio-Medical Materials and Engineering 6, (1996), 307-312, IOS Press.
Office Action issued for corresponding Canadian patent application No. 2,887,570, dated Jan. 19, 2017, 3 pages.

* cited by examiner

US 9,808,296 B2

HAMMERTOE IMPLANT AND INSTRUMENT

CROSS REFERENCE TO RELATED APPLICATIONS

This application is a national phase entry under 35 U.S.C. 371 of international patent application No. PCT/US14/56315, the entirety of which is incorporated herein by reference.

FIELD OF THE INVENTION

This disclosure generally relates to systems and methods for orthopedic surgery. More particularly, this disclosure relates to systems and methods for hammertoe implants.

BACKGROUND

A hammertoe, or contracted toe, is a deformity of the proximal inter-phalangeal joint of the second, third, or fourth toe causing the toe to be permanently bent and giving the toe a semblance of a hammer. Initially, hammertoes are flexible and may be corrected with simple measures but, if left untreated, hammertoes may require surgical intervention for correction. Persons with hammertoe may also have corns or calluses on the top of the middle joint of the toe or on the tip of the toe and may feel pain in their toes or feet while having difficulty finding comfortable shoes.

One method of treatment may include correction by surgery if other non-invasive treatment options fail. Conventional surgery usually involves inserting screws, wires or other similar implants in toes to straighten them. Traditional surgical methods generally include the use of Kirschner wires (K-wires). K-wires require pings protruding through the end of respective toes due to their temporary nature. As a result, K-wires often lead to pin tract infections, loss of fixation, and other conditions. Additional disadvantages of K-wires include migration and breakage of the K-wires thus resulting in multiple surgeries. Due to the various disadvantages of using K-wires, however, compression screws are being employed as an implant alternative.

Screw implants may provide a more permanent solution than K-wires as such implants do not need removal and have no protruding ends. Further, with the use of screw implants, a patient may wear normal footwear shortly after the respective surgery. There are generally two types of known screw implants: single-unit implants, which possess a completely threaded body and do not provide a flexibility to the respective toe in its movement, and articulated or two-unit implants, which typically have one unit that is anchored into the proximal phalanx, a second unit that is anchored into the distal phalanx, and a fitting by which the two units are coupled. Either or both of the two units may be threaded or have other anchoring structures such as barbs or splaying arms.

Among other disadvantages, both kinds of known implants result in an undesirable pistoning effect, i.e., part or all of the implant will toggle or move within the bone as the patient's toe moves. Pistoning decreases the stability of the implant and lessens the compression across the joint. Moving parts, such as fittings, hinges, expansion pieces, and the like also decrease the stability, lifespan, and compression force of the implant. Accordingly, there remains a need for durable hammertoe implants which are not only stable but provide adequate compression across a joint with minimal pistoning. There also remains a need for an implant which can provide these advantages, while being easily inserted with minimal damage to the surrounding tissue.

SUMMARY

The present subject matter relates to a type of bone implant useful in the correction of hammertoe and similar maladies, as well as methods of inserting the implant into bones to effectuate that correction. The bone implant has a number of different embodiments, each of which correspond to different nuances in their respective methods of insertion. All of the hammertoe implant embodiments have an elongate shaft having a first end and a second end coupled by a shaft. The first end is configured to couple to a first bone. The second end comprises an expandable section comprising at least one expandable feature. The expandable feature is configured to be received within a reverse countersink in a second bone in a collapsed state. The first expandable section expands within the reverse countersink such that the at least one expandable feature couples to a bearing surface of the reverse countersink.

In some embodiments, a surgical tool is disclosed. The surgical tool comprises a shaft sized and configured to be received within a canal formed in a bone. At least one expandable cutting edge is formed integrally with the shaft. The expandable cutting edge is configured to expand from a collapsed position for insertion into the canal to an expanded position for forming a reverse countersink in the canal.

In some embodiments a method for correcting a hammertoe is disclosed. The method comprises the steps of forming a first canal in a first bone and forming a second canal in a second bone. A second step of the method comprises inserting a surgical instrument into the second canal. The surgical instrument comprises a shaft, a head located at a first end of the shaft, and an expandable cutting edge formed integrally with the shaft. The expandable cutting edge is deployable from a collapsed position to a deployed position to forming a reverse countersink in the canal. In a third step, the surgical instrument is rotated to form the reverse countersink in the second canal of the second bone.

BRIEF DESCRIPTION OF THE DRAWINGS

The features and advantages of the present invention will be more fully disclosed in, or rendered obvious by the following detailed description of the preferred embodiments, which are to be considered together with the accompanying drawings wherein like numbers refer to like parts and further wherein.

DETAILED DESCRIPTION

Figure 1:
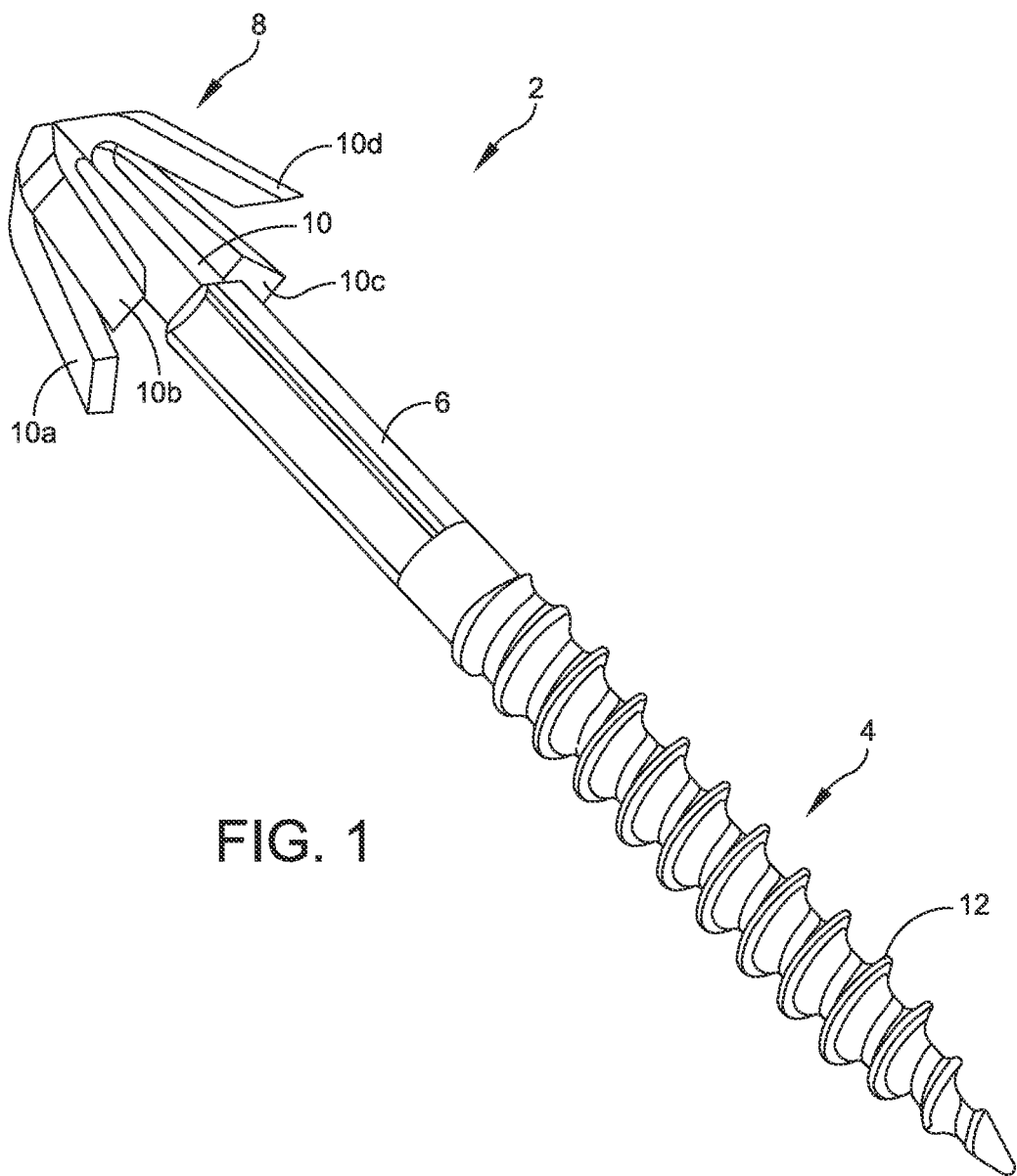
FIG. 1 illustrates one embodiment of a hammertoe implant comprising an expandable section and a threaded section.

The description of the exemplary embodiments is intended to be read in connection with the accompanying drawings, which are to be considered part of the entire written description. In the description, relative terms such as "lower," "upper," "horizontal," "vertical," "above," "below," "up," "down," "top" and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

The present disclosure generally provides a hammertoe implant and instrument for joining a first bone and a second bone, such as, for example, a proximal phalanx and a middle phalanx. The hammertoe implant generally comprises a first end and a second end coupled by a shaft. The first end is configured to couple to the first bone. The second end comprises an expandable section. The expandable section is configured to couple the implant to the second bone. The expandable section expands into a reverse countersink formed in the second bone. The countersink is formed by an instrument generally comprising a shaft having an expandable cutting member formed integrally therein. The expandable cutting member is deployable from a collapsed position to an expanded position configured to form the reverse countersink in the bone.

FIG. 1 illustrates one embodiment of a hammertoe implant 2 comprising a first end 4 and a second end 8 coupled by a shaft 6. The first end 4 is configured to anchor the hammertoe implant 2 to a first bone. For example, in some embodiments, the first end 4 comprises a threaded section 12 configured to be received within a canal formed in a first bone. The threaded section 12 may configured to be inserted into a pre-drilled and/or pre-tapped canal and/or may comprise a self-drilling and/or self-tapping thread. The threaded section 12 may comprise a predetermined length configured to be fully implanted into the first bone. In some embodiments, the first end 4 comprises other suitable mechanisms for coupling the hammertoe implant 2 to the first bone.

The second end 8 comprises an expandable section 10. The expandable section 10 comprises one or more expandable features. For example, in some embodiments, the expandable section 10 comprises a plurality of expandable arms 10a-10d. In other embodiments, the expandable section 10 may comprise, for example, one or more expandable cones, sleeves, threads, or any other suitable expandable feature. The expandable section 10 is configured to transition from a collapsed position to an expanded position. The expandable arms 10a-10d may be arranged in any suitable configuration. For example, the expandable section 10 comprises four expandable arms 10a-10d arranged in a plus-sign configuration having a separation angle between each of the expandable arms 10a-10d of ninety degrees. It will be recognized that other configurations, including fewer or additional expandable arms and/or different angles of separation, are within the scope of the claims.

The first end 4 and the second end 8 are coupled by a shaft 6. The shaft 6 may comprise any suitable cross-section, such as, for example, a cylinder, square, triangle, and/or other suitable cross-section. The shaft 6 comprises a predetermine length. The predetermined length of the shaft 6 may be configured to provide a predetermined spacing between the first bone and the second bone when the hammertoe implant 2 is inserted. In some embodiments, the shaft 6 comprises a predetermined length such that there is substantially no space between the first bone and the second bone after insertion of the hammertoe implant 2.

The hammertoe implant 2 is configured to couple the first bone to the second bone. In some embodiments, the threaded section 12 is inserted into the first bone by rotating the threaded section 12 into contact with the predrilled canal formed in the first bone. The expandable section 10 is received within a cavity in the second bone. The cavity in the second bone comprises a reverse countersink. The expandable arms 10a-10d are configured to couple to a bearing surface of the reverse countersink and maintain the hammertoe implant 2 in the second bone. In some embodiments, the hammertoe implant 2 is configured to join a middle phalanx and a proximal phalanx.

The hammertoe implant 2 may comprise any suitable material or combination of materials. For example, in some embodiments, the hammertoe implant 2 may comprise Nitinol (in either the super-elastic or shape memory state), a Titanium alloy, stainless steel, an equivalent bio-material, and/or any combination thereof. In some embodiments, one or more sections of the hammertoe implant 2, such as the expandable section 10, comprises a first material, for example Nitinol, and a second section of the hammertoe implant 2, such as the threaded section 12, comprises a second material, for example, stainless steel.

Figure 2:
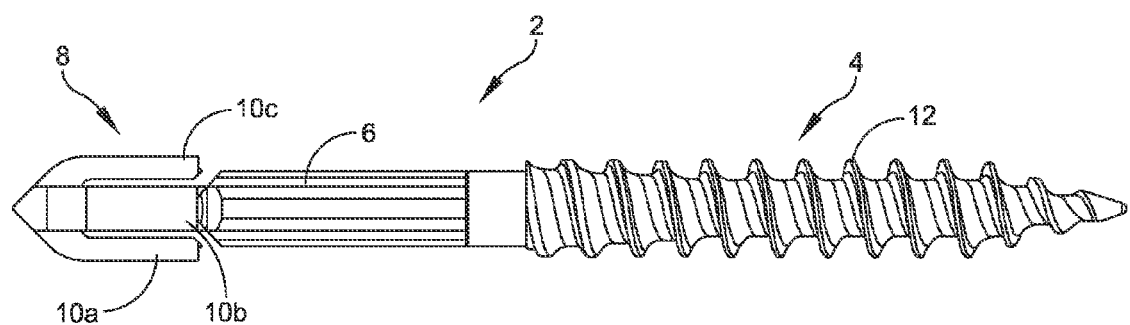
FIG. 2 is a side-view of the hammertoe implant of FIG. 1 having the expandable section in a collapsed state.

FIG. 2 illustrates a side-view of the hammertoe implant 2 of FIG. 1 having the expandable section 10 in a collapsed state. In the collapsed state, the expandable arms 10a-10d are compressed to a first diameter. When the expandable arms 10a-10d are collapsed, the expandable end 10 is sized and configured to be inserted through a canal formed in the second bone. The canal may comprise an internal diameter substantially equal to the first diameter of the expandable section 10. In some embodiments, a sleeve (see FIG. 18) is disposed over the expandable end 10 to maintain the expandable arms 10a-10d in a collapsed state prior to insertion of the expandable section 10 in the second bone. The expandable arms 10a-10d may be maintained in a collapsed state, for example, during insertion of the first end 4 into the first bone.

Figure 3:
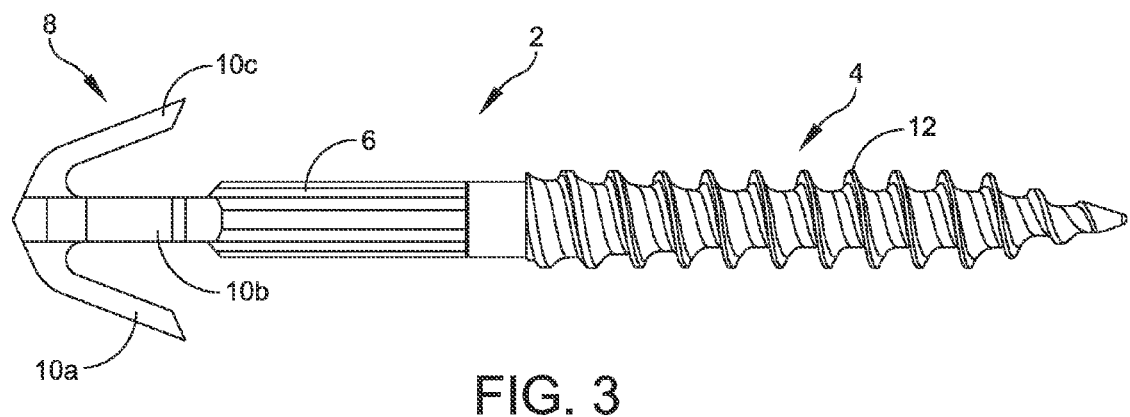
FIG. 3 is a side-view of the hammertoe implant of FIG. 1 having the expandable section in an expanded state.

FIG. 3 illustrates a side-view of the hammertoe implant 2 of FIG. 1 having the expandable section 10 in an expanded, or deployed, state. In the deployed state, the expandable arms 10a-10d are allowed to flare, or expand, out to a second diameter. The second diameter is greater than the diameter of the canal in the second bone. The expandable arms 10a-10d may be biased to an expanded position. In some embodiments, the second diameter is greater than or equal to a diameter of a reverse countersink formed in the second bone. In the expanded state, the expandable arms 10a-10d interface with a bearing surface of the reverse countersink.

Figure 4:
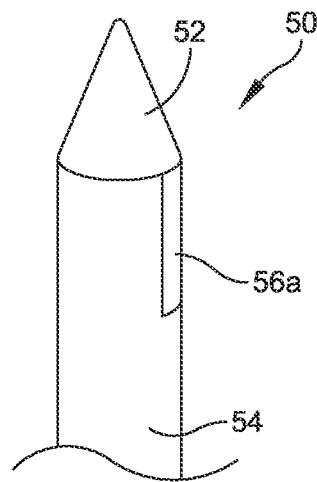
FIG. 4. illustrates one embodiment of a cutting instrument having a deployable cutting section for forming a reverse countersink in a bone.
Figure 5:
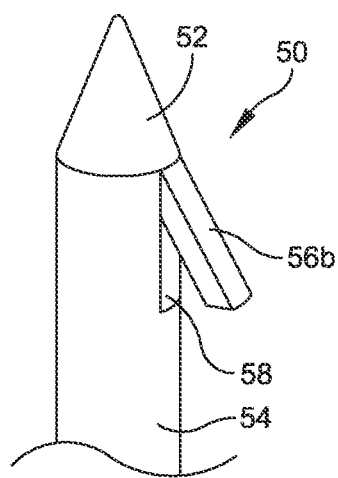
FIG. 5 illustrates the cutting instrument of FIG. 4 having the deployable cutting section in a deployed position.

In some embodiments, the reverse countersink in the second bone is formed by an instrument prior to insertion of the hammertoe implant 2 into the second bone. FIGS. 4 and 5 illustrate one embodiment of an instrument 50 configured to form a reverse countersink in the second bone. The instrument 50 comprises an instrument tip 52 coupled to a shaft 54. The shaft 54 has a cutting edge 56 formed integrally therewith. The cutting edge 56 is deployable from a collapsed state (as shown in FIG. 4) to a deployed state (as shown in FIG. 5). The cutting edge 56 may comprise any suitable deployment mechanism such as, for example, a mechanical deployment mechanism, a hinged deployment mechanism, and/or any other suitable deployment mechanism. The shaft 54 comprises a cavity 58 configured to receive the cutting edge 56 such that the cutting edge 56 is flush with the shaft 54 in a collapsed position. In some embodiments, one or more additional cutting edges 56 may be formed integrally with the shaft 54 and deployed simultaneously. In some embodiments, the diameter of the shaft 54 of the instrument 50 is substantially equal to the diameter of the expandable section 10 of the hammertoe implant 2 in a collapsed position. The cutting edge 56 is configured to form a reverse countersink having a diameter that is substantially equal to or less than a diameter of the expandable section 10 of the hammertoe implant 2 in a deployed position. The reverse countersink provides a bearing surface for the expandable section 10 of the hammertoe implant 2.

Figure 6:
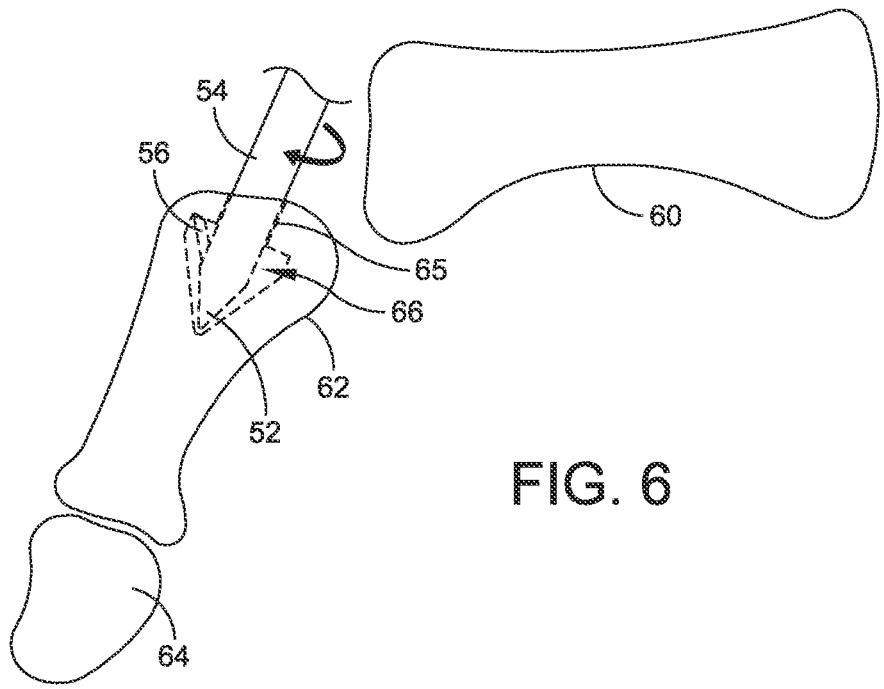
FIG. 6 illustrates one embodiment of the cutting instrument of FIG. 4 inserted into a canal formed in a bone.

FIG. 6 illustrates one embodiment of a second bone 62 having the cutting instrument of FIG. 4 inserted therein. The instrument 50 is inserted into a canal 65 formed in the second bone 62 to a first predetermined depth. The instrument tip 52 and the shaft 54 position the cutting edge 56 at a second predetermined depth in the second bone 62. The cutting edge 56 is deployed from a collapsed position (shown in FIG. 4) suitable for insertion through the canal to a deployed position (shown in FIG. 5). The instrument 50 is rotated about a central axis, causing the cutting edge 56 to form a reverse countersink 66 in the second bone 62. The cutting edge 56 may transition from a partially deployed position to a fully deployed position as bone is removed by the cutting edge 56 during rotation of the instrument 50. Although the cutting edge 56 is configured to form a conical reverse countersink 66, it will be appreciated that the cutting edge 56 may be configured to form any suitable cavity, such as, for example, a conical, square, or cylindrical countersink. After forming the reverse countersink 66, the cutting edge 56 is transitioned from the deployed position to the collapsed position and the instrument 50 is removed from the canal 65.

Figure 7A:
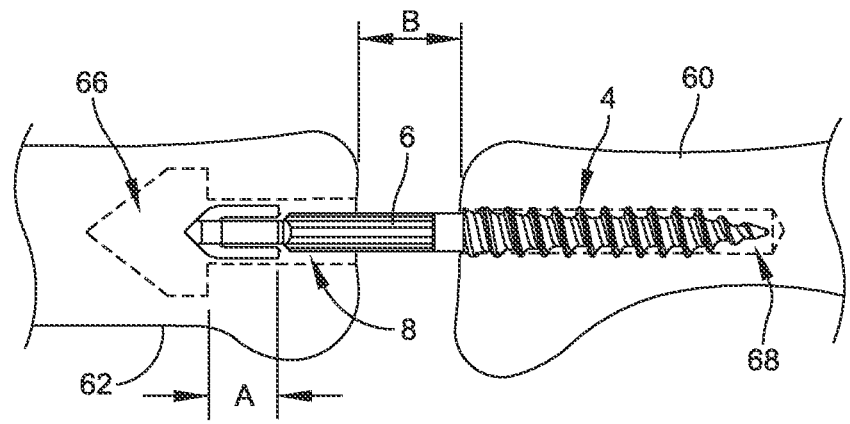
FIG. 7 illustrates one embodiment of the hammertoe implant of FIG. 1 engaging a bone section in a collapsed state.
Figure 7B:
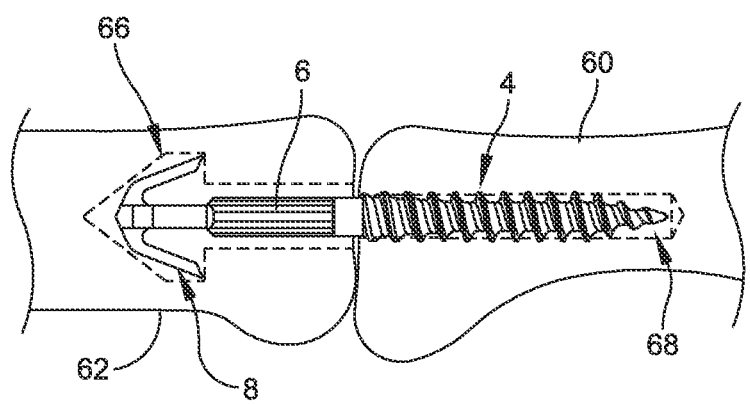

FIG. 7 illustrates the hammertoe implant 2 anchored to the first bone 60 and partially inserted into the second bone 62. The first end 4 of the hammertoe implant 2 is coupled to the first bone 60 by the threaded section 12. The threaded section 12 is inserted into a canal 68 formed in the first bone 60. The canal 68 may be predrilled in the first bone 60 by, for example, a drill, k-wire, and/or other suitable device and/or may be formed by the hammertoe implant 2 during insertion of the threaded section 12. The threaded section 12 extends within the first bone 60 to a predetermined depth. In some embodiments, the threaded section 12 may extend substantially the entire width of the first bone 60. In some embodiments, the threaded section 12 is inserted to a depth such that a portion of the shaft 6 is located within the canal 68. The expandable section 10 is maintained in a collapsed position during insertion of the first end 4 into the first bone 60. The expandable section 10 may be maintained in the collapsed position by, for example, a sleeve (see FIG. 18) disposed over the expandable section 10.

After coupling the hammertoe implant 2 to the first bone 60, the second end 8 of the hammertoe implant 2 is inserted into the second bone 62. The expandable section 10 is inserted into a canal 65 formed in the second bone 62. The canal 65 applies a force to the expandable section 10 that maintains the expandable arms 10a-10d in a collapsed position during insertion and allows the expandable section 10 to traverse the canal 65. A gap exists between the first bone 60 and the second bone 62 as the hammertoe implant 2 has not been fully inserted into the bone 62.

A first length, 'A', illustrates the distance of travel of the expandable end 10 from the initial position illustrated in FIG. 7 bearing surface of the reverse countersink. A second length, 'B', illustrates the corresponding gap between the first bone 60 and the second bone 62. Having a distance 'A' substantially equal to the length 'B' ensures the joint fully closes when the implant 2 is inserted.

Figure 8A:
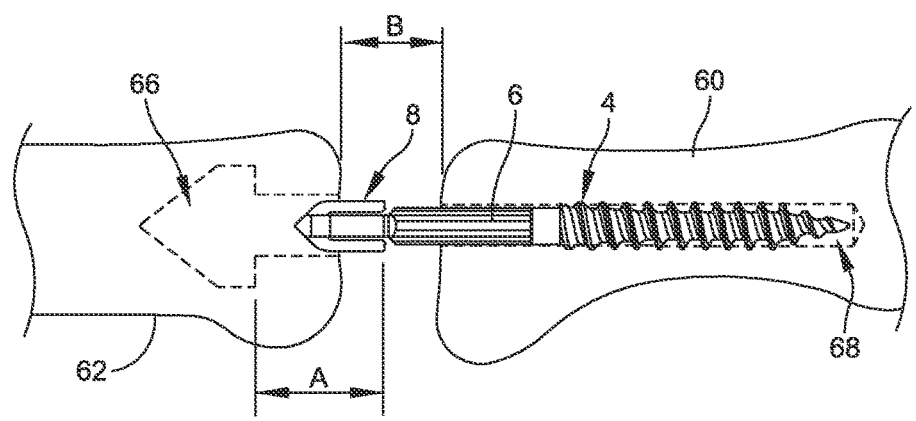
FIG. 8 illustrates one embodiment of the hammertoe implant of FIG. 1 inserted into a reverse countersink.
Figure 8B:
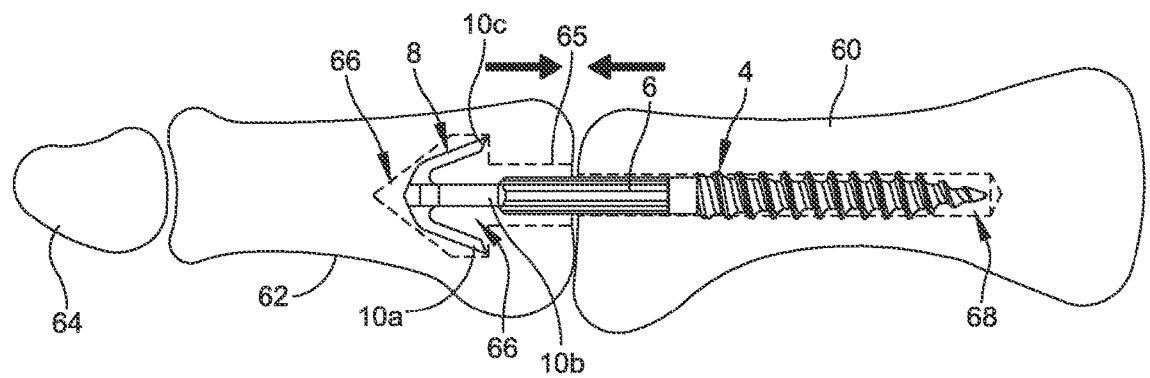

FIG. 8 illustrates the hammertoe implant 2 fully inserted into the second bone 62. The first bone 60 and the second bone 62 are aligned and the joint therebetween is closed, forcing the expandable section 10 into the reverse countersink 66 formed in the second bone 62. As shown in FIG. 8, the expandable arms 10a-10d expand to a deployed position when inserted fully into the reverse countersink 66. The expandable arms 10a-10d have a deployed diameter sufficient to expand beyond the canal 65 and to engage with a bearing surface of the reverse countersink 66. The reverse countersink 66 is sized such that the expandable section 10 fits within the reverse countersink with minimal or no additional space to maintain the hammertoe implant 2 in a fixed position. In some embodiments, the expandable arms 10a-10d comprise an expanded diameter equal to the diameter of the reverse countersink 66. In some embodiments, the expandable arms 10a-10d are biased to a diameter greater than the diameter of the reverse countersink 66, allowing the expandable arms 10a-10d to contact the inner walls of the reverse countersink 66.

Figure 9:
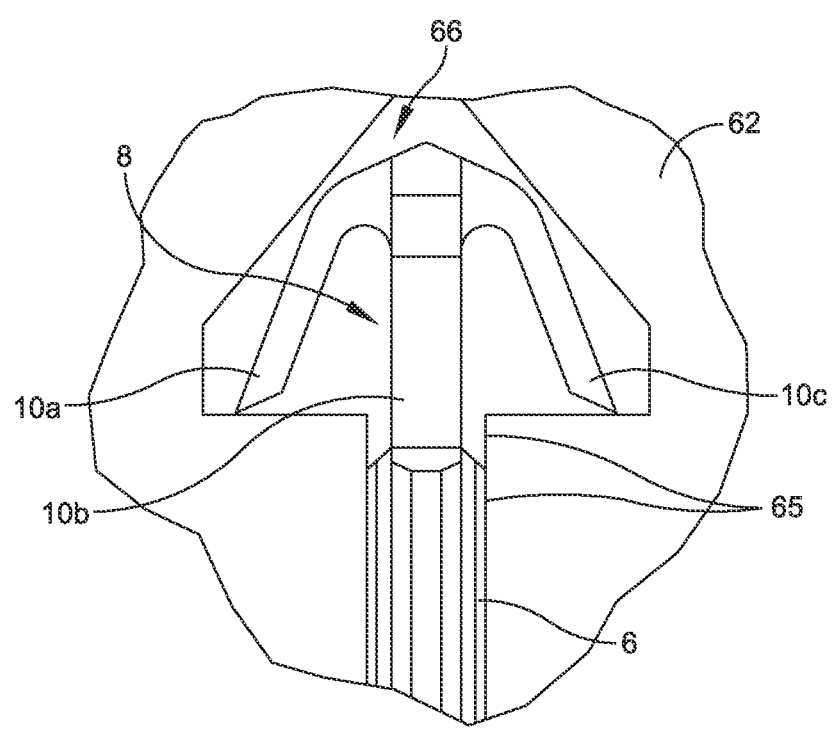
FIG. 9 illustrates an expanded view of a conical countersink having the hammertoe implant of FIG. 1 inserted therein.

FIG. 9 illustrates an isolated view of the expandable section 10 inserted into the reverse countersink 66. As shown, the expandable arms 10a-10d expand to a diameter that is substantially equal to the diameter of the reverse countersink 66. In some embodiments, the expandable arms 10a-10d are biased to a diameter greater than the diameter of the cavity 66 to ensure the expandable arms 10a-10d expand to the full diameter of the countersink 66. The reverse countersink 66 is sized and configured to receive the expandable section 10 with minimal extra space to prevent movement of the hammertoe implant 2 after installation. Although the reverse countersink 66 is shown as a conical cavity, the reverse countersink 66 may comprise any suitable shape corresponding to the shape of the expandable section 10 in an expanded configuration.

With reference to FIGS. 6-9 and 20, a method 600 for coupling a first bone 60 and a second bone 62 is discussed. In a first step 602, a canal 68 is formed in the first bone 60. The canal 68 is sized and configured to receive a first end 4 of an hammertoe implant 2. In a second step 604, a canal 65 is formed in the second bone 62. The canal 65 in the second bone 62 is sized and configured to receive an instrument 50 therein. The instrument 50 is configured to form a reverse countersink 66 in the second bone 62. The canal 68 in the first bone 60 and/or the canal 65 in the second bone 62 may be formed using, for example, a k-wire, a drill and/or any other suitable device. In some embodiments, the first bone 60 comprises a proximal phalanx, the second bone 62 comprises a middle phalanx.

In a third step 606, the instrument 50 is inserted into the canal 65 formed in the second bone 62. The instrument 50 comprises an instrument tip 52 and a shaft 54. The instrument 50 is inserted to a first predetermined depth in the canal 65. In some embodiments, the instrument 50 is inserted until the instrument tip 52 contacts a closed end of the canal. In other embodiments, the instrument tip 52 is inserted to a first predetermined depth indicated on the instrument 52. A deployable cutting edge 56 is coupled to the shaft 54. The instrument tip 52 and the shaft 54 are configured to locate the cutting edge 56 at a second predetermined depth within the canal 65. In a fourth step 608, the cutting edge 56 is deployed and the instrument 50 is rotated about a central axis to form a reverse countersink 66 within the second bone during a fourth step 608. After forming the reverse countersink 66, the cutting edge 56 is collapsed against the shaft 54 and, in a fifth step 610, the instrument 50 is removed from the canal 65.

In a sixth step 612, a sleeve (see FIG. 18) is placed over an expandable section 10 of a hammertoe implant 2. The sleeve is configured to compress the expandable section 10 and to provide a handle for rotating the hammertoe implant 2. In some embodiments, the sixth step 612 is omitted. In a seventh step 614, the first end 4 of the hammertoe implant 2 is inserted into the canal 68 formed in the first bone 60. The hammertoe implant 2 may be inserted by, for example, rotatably interfacing the threaded section 12 with the canal 68. The hammertoe implant 2 is inserted to a predetermined depth in the first bone 60. The predetermined depth may correspond to a length of the threaded section 12. In some embodiments, the threaded section 12 is configured to extend substantially through the entire width of the first bone 60. In some embodiments, a portion of the shaft 6 is inserted into the canal 68.

After the first end 4 is inserted into the first bone 60, the second end 4 of the hammertoe implant 2 is inserted into the second bone 62 during an eighth step 616. If a sleeve was disposed over the expandable section 10 to maintain the expandable arms 10a-10d in a collapsed position, the sleeve is removed prior to insertion of the second end 4 into the second bone. In some embodiments, the expandable arms 10a-10d are biased to an expanded position.

The expandable section 10 is inserted into the canal 65 formed in the second bone 62. The canal 65 exerts a force on the expandable arms 10a-10d and forces the expandable arms 10a-10d into a collapsed position. In the collapsed position, the expandable section 10 is sized and configured to fit through the canal 65. For example, in some embodiments, the expandable arms 10a-10d have a diameter in a collapsed position equal to or less than an internal diameter of the canal 65. The expandable section 10 is inserted through the canal 65 to the reverse countersink 66 formed in the second bone 62. In a ninth step 618, the expandable arms 10a-10d assume an expanded configuration, as shown in FIGS. 8-9. The expandable arms 10a-10d interface with a bearing surface of the reverse countersink 66 formed in the second bone 62. In some embodiments, the reverse countersink 66 and the expandable section 10 of the hammertoe implant 2 are sized and configured to prevent movement of the hammertoe implant 2 after insertion of the expandable head 10 into the reverse countersink 66.

Figure 10:
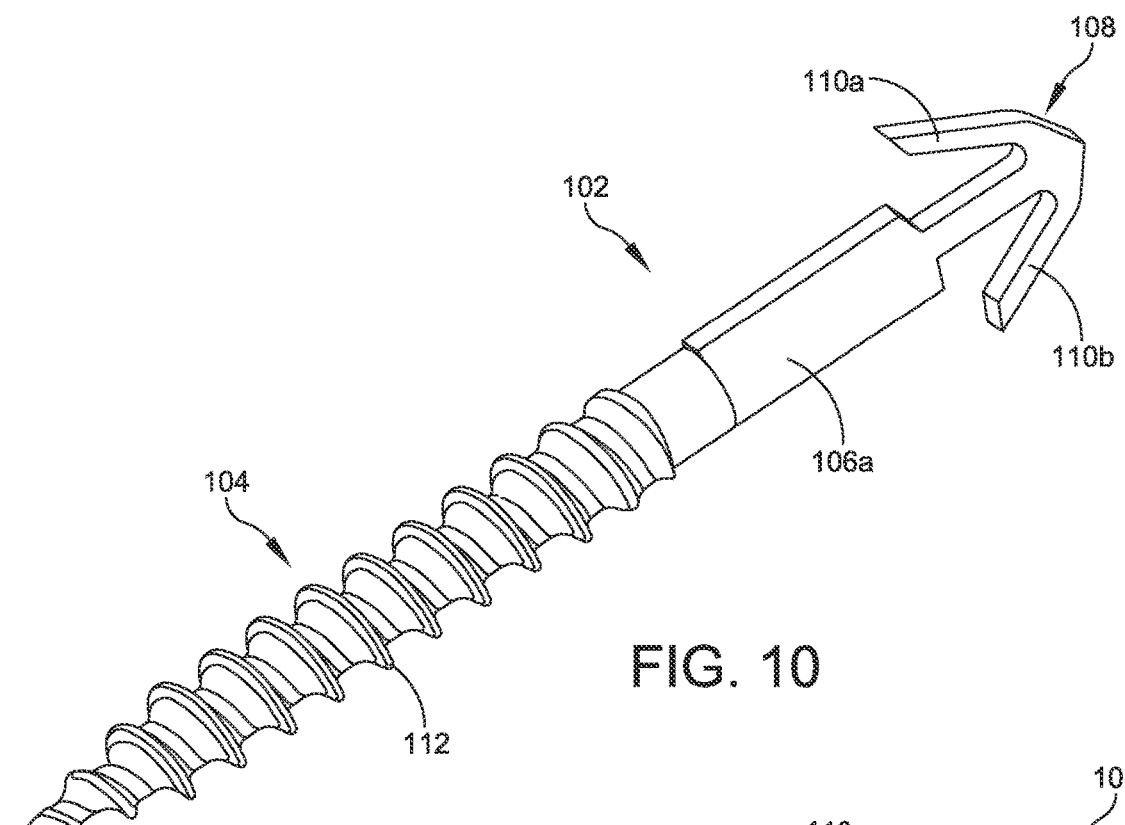
FIG. 10 illustrates one embodiment of a hammertoe implant comprising an expandable section having a first arm and a second arm.
Figure 11:
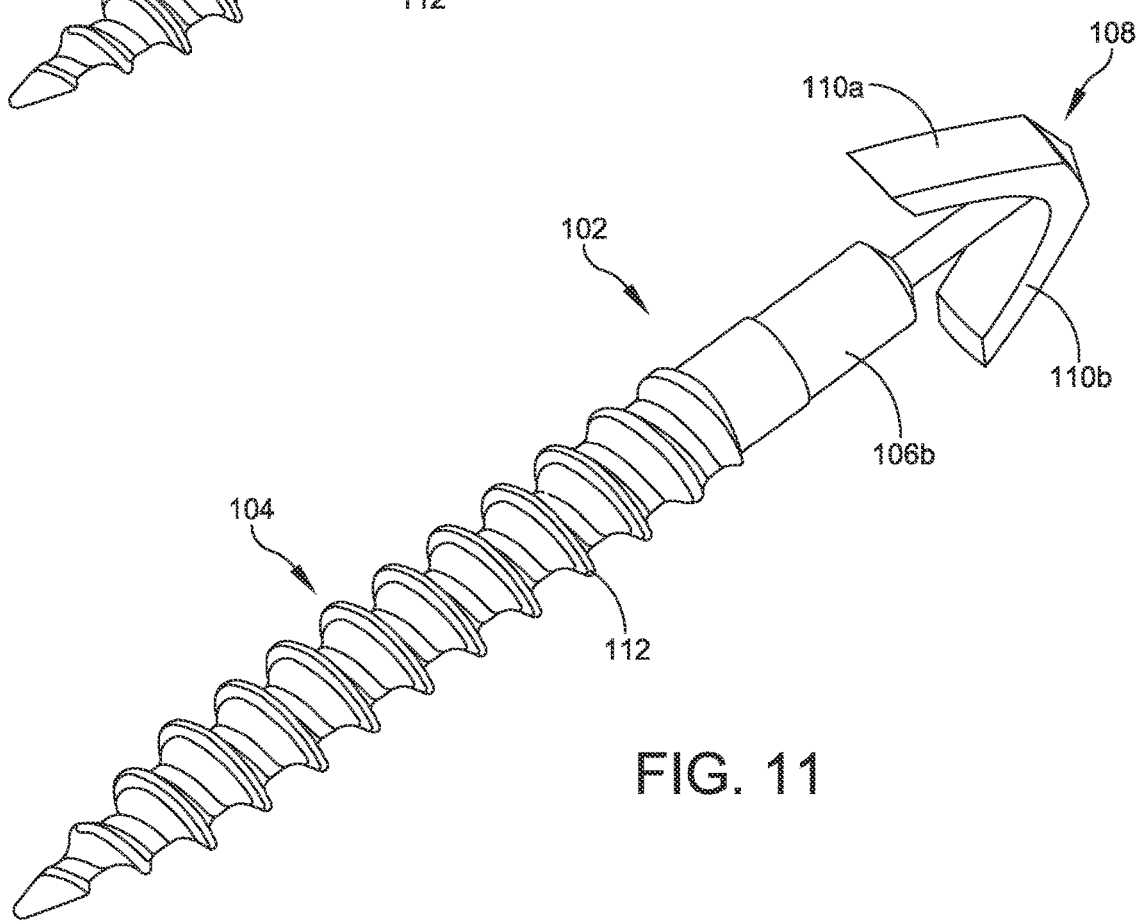
FIG. 11 illustrates one embodiment of a hammertoe implant comprising a cylindrical shaft section.

FIGS. 10-16 illustrate additional embodiments of implants for joining a first bone 60 and a second bone 62. FIGS. 10 and 11 illustrate one embodiment of an implant 102 comprising an expandable section 110 having a first expandable arm 110a and a second expandable arm 110b. In other aspects, the implant 102 is similar to the hammertoe implant 2 described in conjunction with FIGS. 1-9. The implant 102 is configured to couple a first bone 60 and a second bone 62, for example, a proximal phalanx and a middle phalanx. FIG. 10 illustrates one embodiment of an implant 102 having a square shaft 106a. FIG. 11 illustrates one embodiment of an implant 102 having a cylindrical shaft 106b. Those skilled in the art will recognize that the shaft 106 may comprise any suitable cross-sectional shape.

Figure 12:
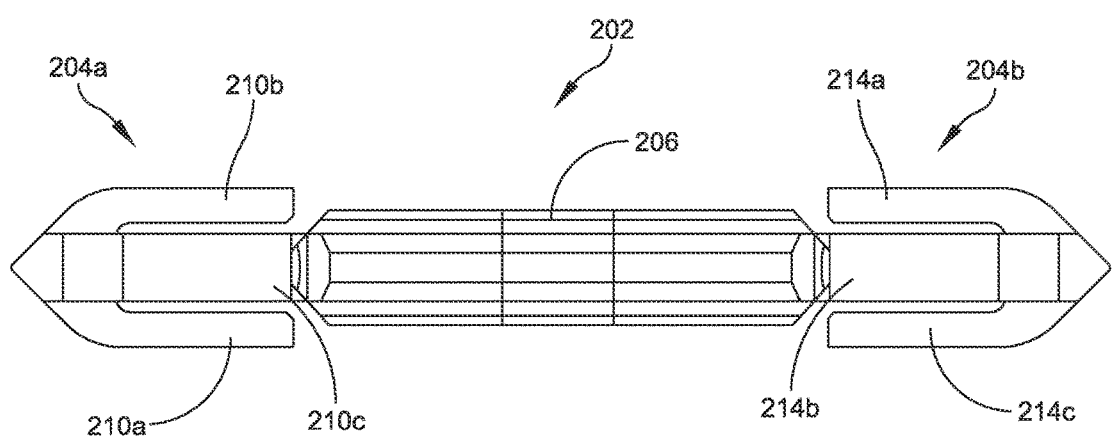
FIG. 12 illustrates one embodiment of a hammertoe implant having a first expandable section and a second expandable section.
Figure 13:
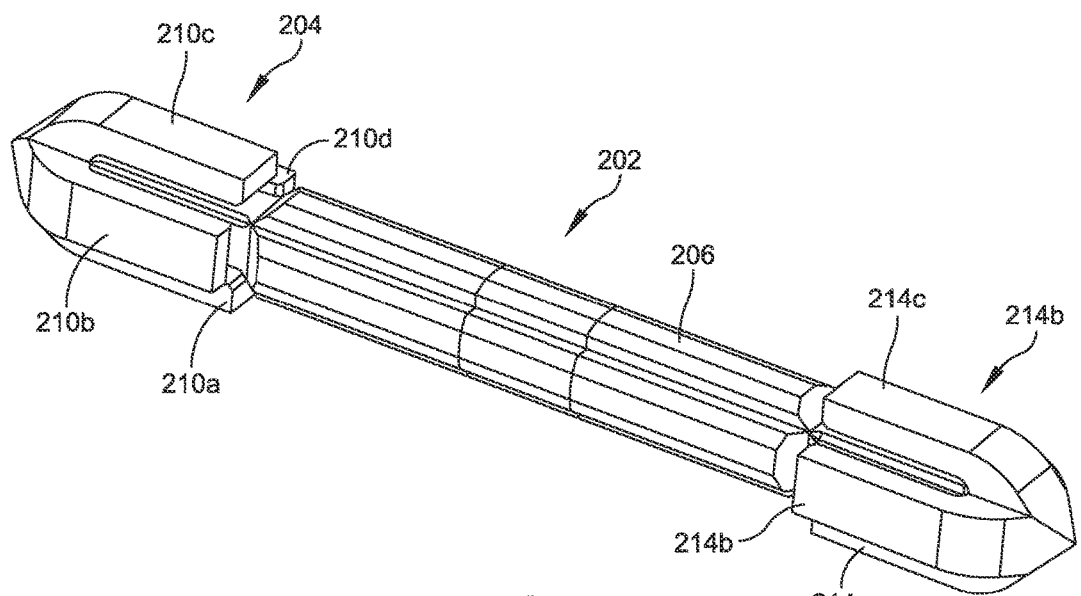
FIG. 13 is a perspective view of the hammertoe implant of FIG. 12 in a collapsed state.
Figure 14:
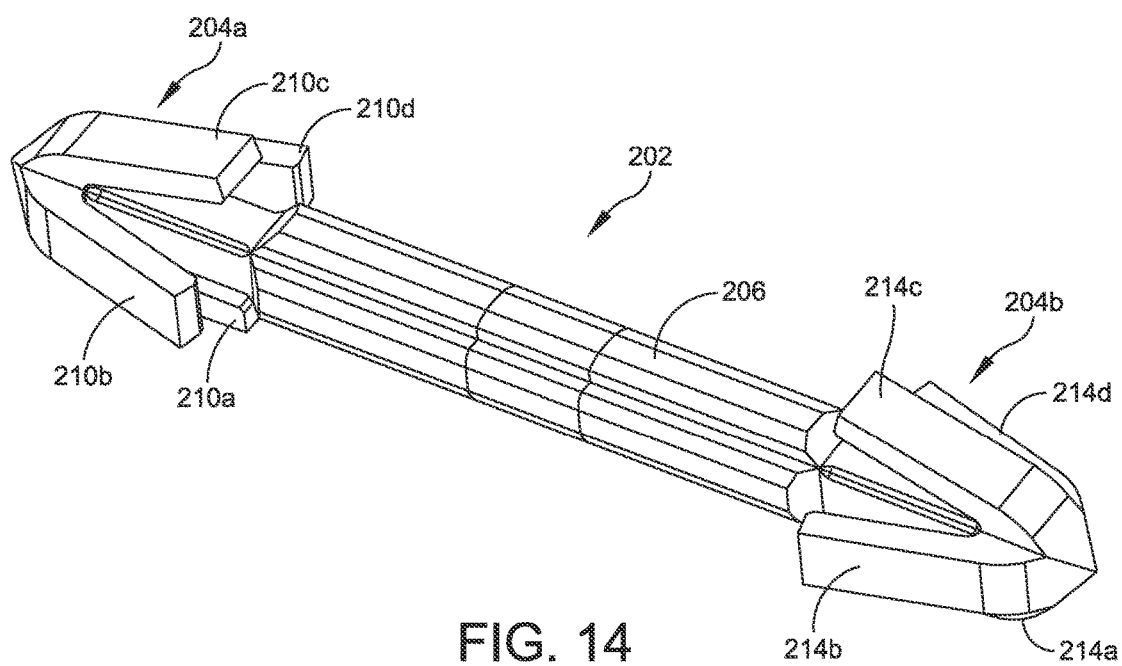
FIG. 14 is a perspective view of the hammertoe implant of FIG. 12 in an expanded state.
Figure 15:
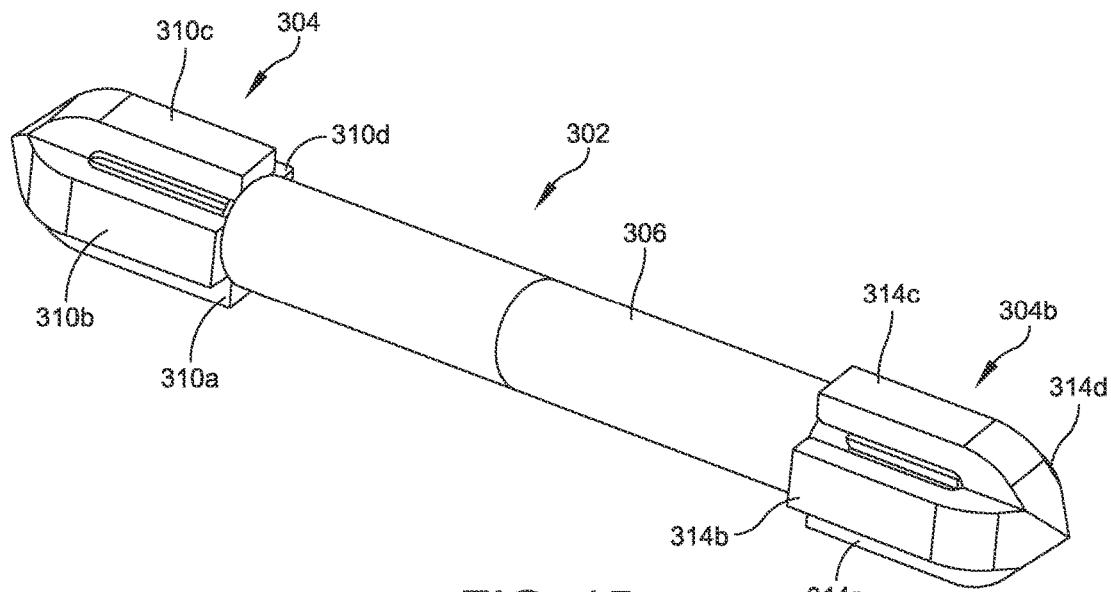
FIG. 15 illustrates one embodiment of a hammertoe implant having a first expandable section, a second expandable section, and a cylindrical shaft.
Figure 16:
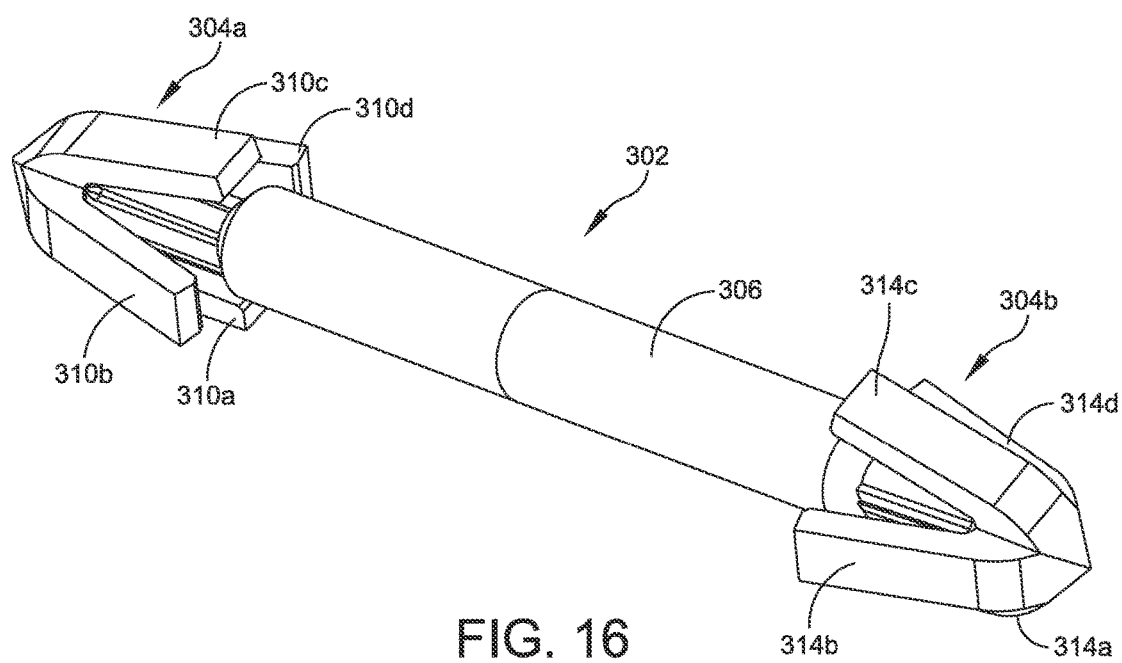
FIG. 16 is a perspective view of the hammertoe implant of FIG. 15 in an expanded state.

FIGS. 12-16 illustrate embodiments of hammertoe implants 202, 302 comprising a first expandable section 204a, 304a and a second expandable section 204b, 304b coupled by a shaft 206, 306. FIGS. 12-14 illustrate one embodiment of an implant 202 having a first expandable section 204a and a second expandable section 204b coupled by a square shaft 206. Each of the first and second expandable sections 204a, 204b comprise a plurality of expandable arms 210a-210d, 214a-214d. The expandable arms 210a-210d, 214a-214d are illustrated in a collapsed position in FIGS. 12 and 13. FIG. 14 illustrates the expandable arms 210a-210d, 214a-214d in an expanded position. The expandable sections 204a, 204b are similar to the expandable section 10 discussed with respect to FIGS. 1-9. FIGS. 15 and 16 illustrate one embodiment of an implant 302 comprising a first expandable section 304a and a second expandable section 304b coupled by a cylindrical shaft 306. Each of the expandable sections 304a, 304b comprise a plurality of expandable arms 310a-310d, 314a-314d.

Figure 17:
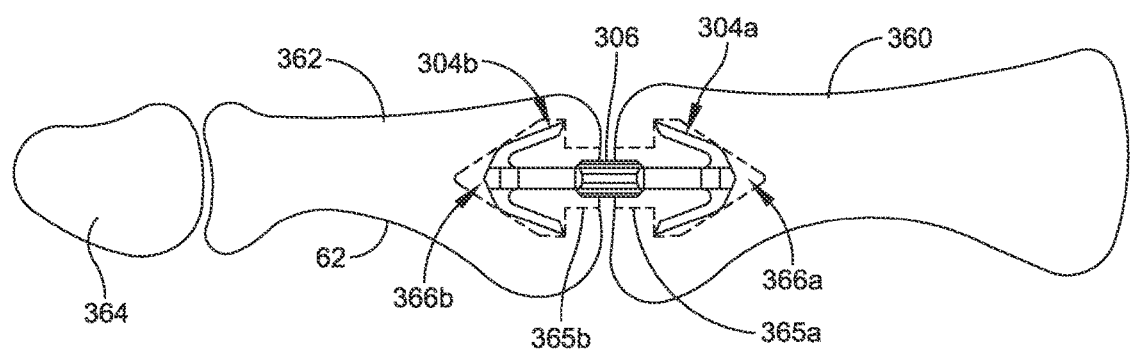
FIG. 17 illustrates the hammertoe implant of FIG. 15 inserted into a first bone and a second bone.

The implants 202, 302 are configured to join a first bone to a second bone, such as, for example, a middle phalanx to a proximal phalanx. FIG. 17 illustrates one embodiment of the implant 302 coupling a first bone 360 and a second bone 364. Canals 365a, 365b comprising reverse countersinks 366a, 366b are formed in each of the first bone 360 and the second bone 362. The reverse countersinks 366a, 366b may be formed by, for example, the instrument 50 described in conjunction with FIGS. 4-6. The first end 304a of the implant 302 is inserted into the canal 365a of the first bone 360 in a collapsed state. In some embodiments, the canal 365a exerts a force on the expandable arms 310a-310d, maintaining the expandable arms 310a-310d in a collapsed position sized and configured to slideably transition through the canal 365a. When the expandable section 304a reaches the reverse countersink 366a, the expandable arms 310a-310d expand and engage a bearing surface of the reverse countersink 366a to maintain the implant 302 in the first bone 360.

The second expandable section 304b of the implant 302 is inserted into the canal 365b formed in the second bone 362. The canal 365b comprises a reverse countersink 366b. The second end 304b of the implant 302 is inserted into the canal 365b of the second bone 362 in a collapsed state. In some embodiments, the canal 365b forces the expandable arms 314a-314d into a collapsed state during insertion of the implant 302 to allow the second end 304b to traverse the canal 365b. When the second expandable section 304b reaches the reverse countersink 366b, the expandable arms 314a-314d expand to a deployed position and engage a bearing surface of the reverse countersink 366b. The first bone 360 and the second bone 362 are aligned and maintained by the implant 302.

With reference to FIGS. 12-17 and 21, a method 650 for coupling a first bone 60 and a second bone 62 is discussed. In a first step 652, a canal 68 is formed in the first bone 60. In a second step 654, a canal 65 is formed in the second bone 62. The canals 65 and 68 are sized and configured to receive an instrument 50 therein. The instrument 50 is configured to form a reverse countersink 66 in each of the first bone 60 and the second bone 62. The canal 68 in the first bone 60 and/or the canal 65 in the second bone 62 may be formed using, for example, a k-wire, a drill and/or any other suitable device. In some embodiments, the first bone 60 comprises a proximal phalanx, the second bone 62 comprises a middle phalanx.

In a third step 656, the instrument 50 is inserted into the canal 65 formed in the second bone 62. The instrument 50 comprises an instrument tip 52 and a shaft 54. The instrument 50 is inserted to a first predetermined depth in the canal 65. In some embodiments, the instrument 50 is inserted until the instrument tip 52 contacts a closed end of the canal. In other embodiments, the instrument tip 52 is inserted to a first predetermined depth indicated on the instrument 52. A deployable cutting edge 56 is coupled to the shaft 54. The instrument tip 52 and the shaft 54 are configured to locate the cutting edge 56 at a second predetermined depth within the canal 65. In a fourth step 658, the cutting edge 56 is deployed and the instrument 50 is rotated about a central axis to form a reverse countersink 66 within the second bone during a fourth step 608. After forming the reverse countersink 66, the cutting edge 56 is collapsed against the shaft 54 and, in a fifth step 660, the instrument 50 is removed from the canal 65. In a sixth step 662, the instrument is inserted into the canal 68 formed in the first bone 60, the deployable cutting edge 56 is deployed, and a reverse countersink is formed in the first bone 60. The deployable cutting edge 56 is collapsed against the shaft 54 after forming the reverse countersink in the first bone and the instrument 50 is removed from the first bone 60.

In a seventh step 664, a sleeve (see FIG. 18) is placed over the second expandable section 214 of a hammertoe implant 202. The sleeve is configured to compress the second expandable section 214 and to provide a handle for gripping the hammertoe implant 2. In some embodiments, the sixth step 612 is omitted. In an eighth step 666, the first expandable end 210 of the hammertoe implant 2 is inserted into the canal 68 formed in the first bone 60. The canal 68 exerts a force on the expandable arms 210a-210d and forces the expandable arms 210a-210d into a collapsed position. In the collapsed position, the expandable section 210 is sized and configured to fit through the canal 68. For example, in some embodiments, the expandable arms 210a-210d have a diameter in a collapsed position equal to or less than an internal diameter of the canal 68. The expandable section 210 is inserted through the canal 68 to the reverse countersink formed in the first bone 60. In a ninth step 668, the expandable arms 210a-210d assume an expanded configuration. The expandable arms 210a-210d interface with a bearing surface of the reverse countersink formed in the first bone 60. In some embodiments, the reverse countersink and the expandable section 210 of the hammertoe implant 202 are sized and configured to prevent movement of the hammertoe implant 202 after insertion of the expandable head 210 into the reverse countersink.

After the first expandable section 210 is inserted into the first bone 60, the second expandable section 214 of the hammertoe implant 202 is inserted into the second bone 62 during a tenth step 670. If a sleeve was disposed over the expandable section 214 to maintain the expandable arms 214a-214d in a collapsed position, the sleeve is removed prior to insertion. In some embodiments, the expandable arms 214a-214d are biased to an expanded position.

The second expandable section 214 is inserted into the canal 65 formed in the second bone 62. The canal 65 exerts a force on the expandable arms 214a-214d and forces the expandable arms 214a-214d into a collapsed position. In the collapsed position, the second expandable section 214 is sized and configured to fit through the canal 65. For example, in some embodiments, the expandable arms 214a-214d have a diameter in a collapsed position equal to or less than an internal diameter of the canal 65. The second expandable section 214 is inserted through the canal 65 to the reverse countersink 66 formed in the second bone 62. In an eleventh step 672, the expandable arms 214a-214d assume an expanded configuration. The expandable arms 214a-214d interface with a bearing surface of the reverse countersink 66 formed in the second bone 62. In some embodiments, the reverse countersink 66 and the second expandable section 214 of the hammertoe implant 202 are sized and configured to prevent movement of the hammertoe implant 202 after insertion of the second expandable section 214 into the reverse countersink 66.

Figure 18:
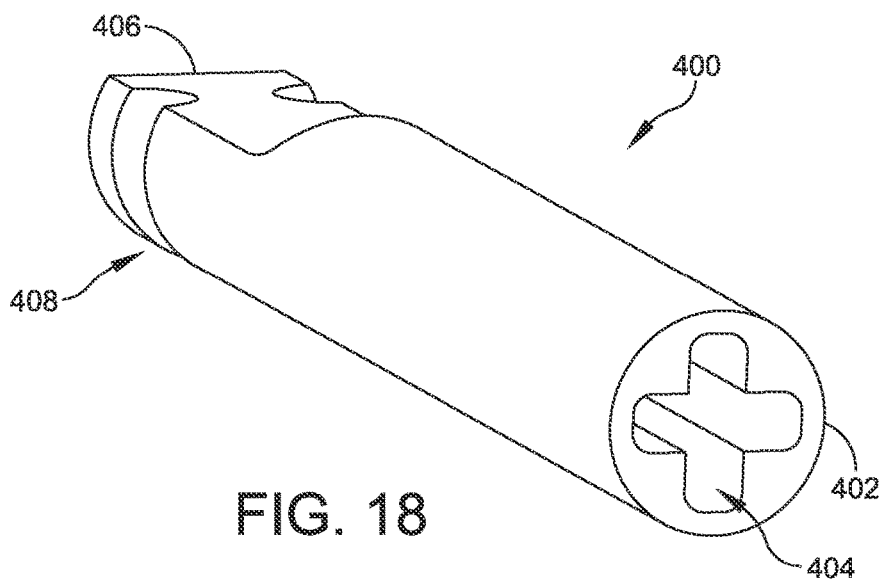
FIG. 18 illustrates one embodiment of a combination sleeve and driver configured to insert the hammertoe implant of FIG. 1.
Figure 19:
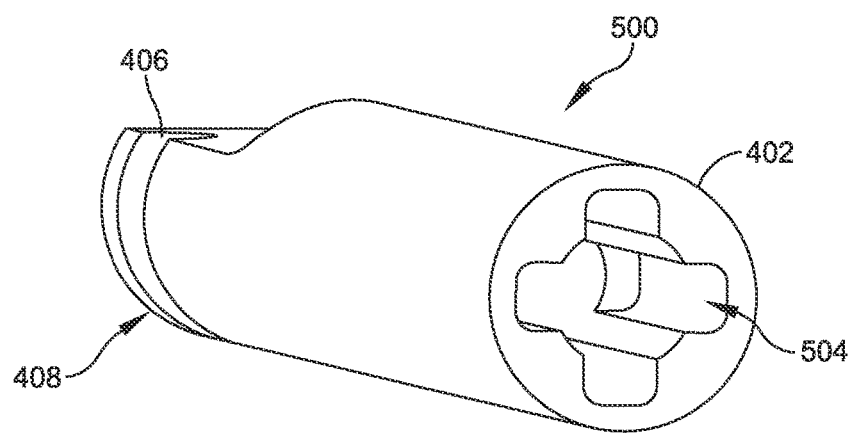
FIG. 19 illustrates one embodiment of a combination sleeve and driver configured to insert the hammertoe implant of FIG. 1.
Figure 20:
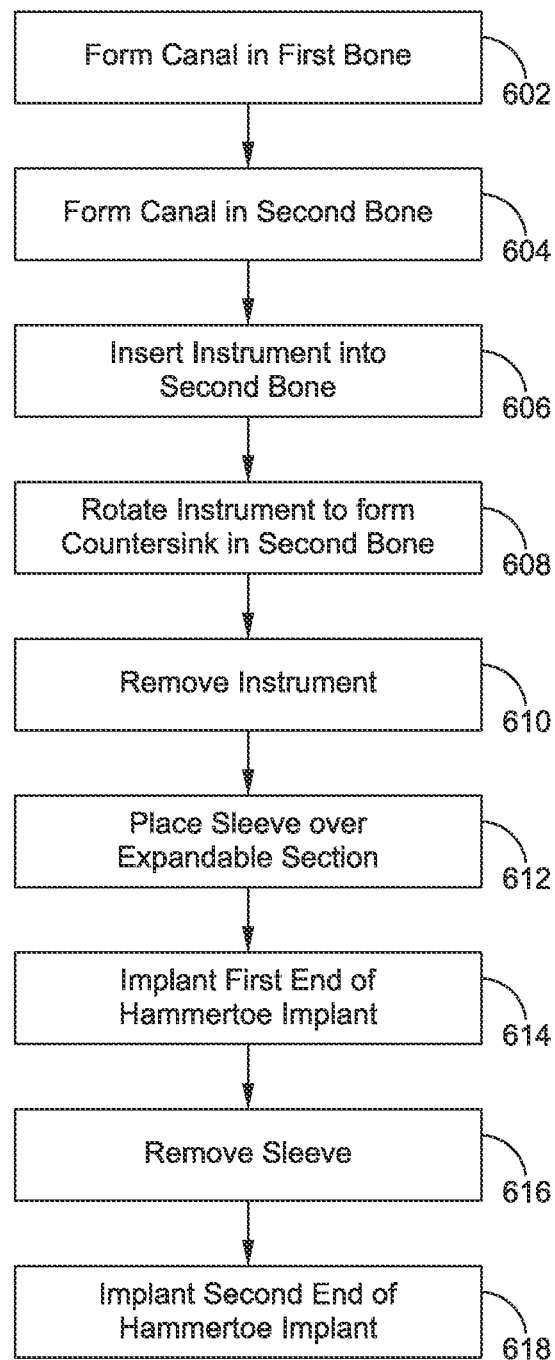
FIG. 20 illustrates a method of treating a hammertoe using a hammertoe implant.
Figure 21:
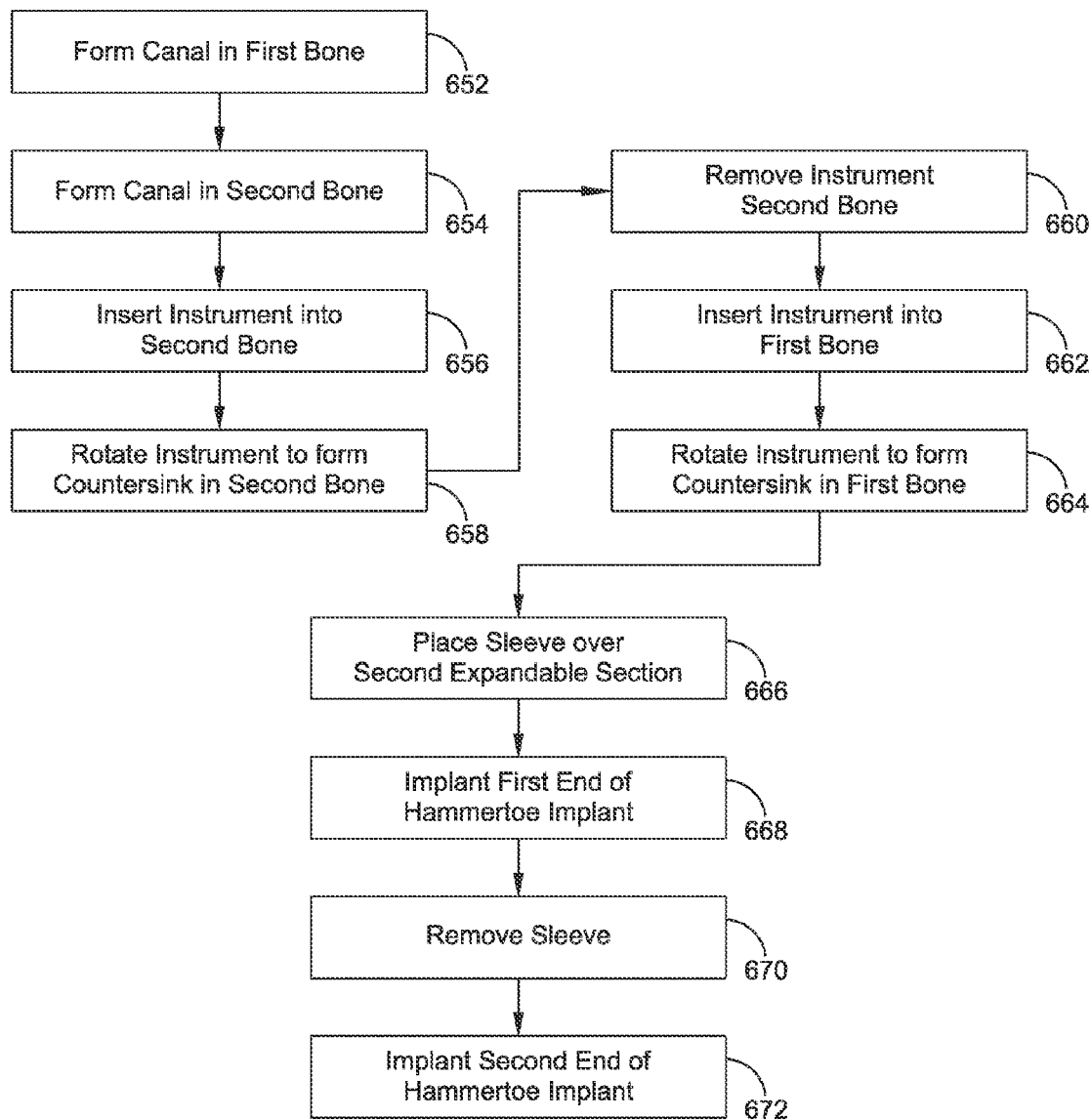
FIG. 21 illustrates a method of treating a hammertoe using a hammertoe implant.

FIG. 18 illustrates one embodiment of a combination sleeve and driver configured to insert one or more embodiments of the hammertoe implant. For example, in some embodiments, the combination sleeve and driver 400 is configured for use with the hammertoe implants 2, 102, 202, 302 illustrated in FIGS. 1-17. The combination sleeve and driver 400 comprises a longitudinal sleeve 402 defining a channel 404 configured to receive an expandable section 10 of an implant 2. The expandable features 10a-10d of the expandable section 10 are compressed against the implant 2 by the channel 404 and maintained in a collapsed position. The combination sleeve and driver 400 comprises a driver head 406. The driver head 406 may comprise a quick connect feature 408 configured to attach the combination sleeve and driver 400 to a handle to drive the implant 2. The quick connect feature 408 and the handle may be configured to provide translation, rotation, and/or any other suitable movement to couple the first end 4 to the first bone. In some embodiments, the internal mating features of the channel 404 provide rotational control such that the implant 2 can be driver proximally or backed out distally. For example, in one embodiment, the expandable features 10a-10d and the channel 404 operate as an inverted Phillips head interface. FIG. 19 illustrates an alternative embodiment of a combination sleeve and driver 500. In the embodiment of FIG. 19, the channel 504 comprises a wider opening and rounded edges to accommodate the expandable features 10a-10d of the expandable side 10.

In some embodiments, a bone implant is disclosed. The bone implant comprises a first end configured to couple to a first bone, a second end defining a first expandable section comprising at least one expandable feature, and an elongate shaft extending longitudinally between the first end and the second end. The first expandable section is sized and configured to be received within a reverse countersink formed in a second bone in a collapsed state. The first expandable section expands within the reverse countersink such that the at least one expandable feature couples to a bearing surface of the reverse countersink.

In some embodiments, the first expandable section comprises a plurality of expandable arms.

In some embodiments, the expandable section comprises four expandable arms.

In some embodiments, the first end comprises a threaded section.

In some embodiments, the threaded section comprises a length sufficient to extend through a thickness of the first bone.

In some embodiments, the first end defines a second expandable section comprising at least one expandable feature. The second expandable section is configured to be received within a reverse countersink formed in the first bone in a collapsed state. The second expandable section expands within the reverse countersink such that the at least one expandable feature couples to a bearing surface of the reverse countersink.

In some embodiments, the second expandable section comprises a plurality of expandable arms.

In some embodiments, the first expandable section comprises a material selected from the group consisting of: Nitnol, titanium, alloy, and stainless steel.

In some embodiments, the first bone comprises a proximal phalanx and the second bone comprises a middle phalanx.

In some embodiments, the elongate shaft extends a predetermined length such that when the first end is fully inserted into the first bone and the second end is fully inserted into the second bone there is substantially no gap between the first and second bones.

In some embodiments, a surgical tool is disclosed. The surgical tool comprises a shaft sized and configured to be received within a canal formed in a bone and at least one expandable cutting edge formed integrally with the shaft. The expandable cutting edge comprises a collapsed position configured for insertion into the canal and an expanded position configured to form a reverse countersink in the canal. The expandable cutting edge is deployed to the expanded position after being inserted into the canal.

In some embodiments, the surgical tool comprises a conical head configured to contact an end of the canal and to space the expandable cutting edge a predetermined distance from the end of the canal.

In some embodiments, the at least one expandable cutting edge is deployed by mechanical deflection.

In some embodiments, the at least one expandable cutting edge comprises a hinge.

In some embodiments, the at least one expandable cutting edge is configured to form the reverse countersink when the shaft is rotated.

In some embodiments, a method for correcting hammertoe is disclosed. The method comprises the steps of forming a first canal in a first bone, forming a second canal in a second bone, inserting a surgical instrument into the second canal, and rotating the surgical tool to form a reverse countersink in the second canal of the second bone. The surgical instrument comprises a shaft, a head located at a first end of the shaft, and an expandable cutting edge formed integrally with the shaft and deployable from a collapsed position to an expanded position.

In some embodiments, the method further comprises inserting a first end of an implant into the first canal in the first bone.

In some embodiments, the method further comprises inserting an second end of an implant into the second canal in the second bone. The second end of the implant comprises an expandable section wherein the expandable section comprises at least one expandable feature. The expandable section is inserted through the second canal to the reverse countersink in a collapsed position. The at least one expandable feature expands within the reverse countersink such that the at least one expandable feature couples to a bearing surface of the reverse countersink.

In some embodiments, the canal exerts a force on the expandable section to maintain the expandable section in a collapsed state during insertion. The at least one expandable feature deploys when fully inserted into the reverse countersink.

In some embodiments, the first end of the implant comprises a threaded section.

Inserting the first end of the implant comprises rotating the threaded section into engagement with the first canal.

In some embodiments, a method for correcting hammertoe is disclosed. The method comprises the steps of forming a first canal in a first bone, forming a second canal in a second bone, and inserting a surgical instrument into the first canal. The surgical instrument comprises a shaft, a head located at a first end of the shaft, and an expandable cutting edge formed integrally with the shaft and deployable from a collapsed position to an expanded position. The method further comprises rotating the surgical tool to form a reverse countersink in the first canal of the first bone, inserting the surgical instrument into the second canal, and rotating the surgical tool to form a reverse countersink in the second canal of the second bone.

In some embodiments, the method further comprises inserting a first end of an implant into the first canal in the first bone. The first end of the implant comprising a first expandable section having at least one expandable feature. The first expandable section is inserted through the first canal to the reverse countersink in a collapsed position. The at least one expandable feature expands within the reverse countersink such that the at least one expandable feature couples to a bearing surface of the reverse countersink.

In some embodiments, the first canal exerts a force on the first expandable section to maintain the first expandable section in a collapsed state during insertion. The at least one expandable feature deploys when fully inserted into the reverse countersink.

In some embodiments, the method further comprises inserting a second end of the implant into the second canal in the second bone. The second end of the implant comprises a second expandable section having at least one expandable feature. The second expandable section is inserted through the second canal to the reverse countersink in a collapsed position. The at least one expandable feature expands within the reverse countersink such that the at least one expandable feature couples to a bearing surface of the reverse countersink.

In some embodiments, the second canal exerts a force on the second expandable section to maintain the second expandable section in a collapsed state during insertion. The at least one expandable feature deploys when fully inserted into the reverse countersink.

Although the subject matter has been described in terms of exemplary embodiments, it is not limited thereto. Rather, the appended claims should be construed broadly, to include other variants and embodiments, which may be made by those skilled in the art.

What is claimed is:

1. A bone implant system, comprising:
    a bone implant having:
        a first end configured to couple to a first bone;
        a second end;
        a first expandable section comprising at least one expandable feature, wherein the first expandable section is sized and configured to be received within a reverse countersink formed in a second bone in a collapsed state, wherein the first expandable section is configured to expand within the reverse countersink such that the at least one expandable feature couples to a bearing surface of the reverse countersink, wherein the at least one expandable feature comprises a plurality of expandable arms each having a connection end and a free end, the connection end coupled to a distal portion of the second end and the free end being proximally disposed relative to the connection end to couple to the bearing surface of the reverse countersink, wherein the free ends of the plurality of expandable arms define a first diameter when in a collapsed state and a second diameter when fully expanded, and further wherein the countersink defines a countersink diameter, the second diameter being equal to or greater than the countersink diameter; and
        an elongate shaft extending longitudinally between the first end and the second end, wherein a proximal portion of the second end is coupled to the elongate shaft; and
    a driver comprising a longitudinal sleeve having a channel configured to receive the expandable section of the second end for controlling rotation of the bone implant.

2. The bone implant of claim 1, wherein the channel has a reverse Phillips head interface for collapsing the expandable arms.

3. The bone implant of claim 2, wherein the expandable section comprises four expandable arms and the channel has a reverse Phillips head interface for collapsing the expandable arms.

4. The bone implant of claim 2, wherein the driver has a quick connect feature at an end opposite the reverse Phillips head interface, the quick connect feature configured to be attached to a handle for driving the bone implant.

5. The bone implant of claim 1, wherein the first end comprises a threaded section.

6. The bone implant of claim 1, wherein the first end defines a second expandable section comprising at least one expandable feature, wherein the second expandable section is configured to be received within a reverse countersink formed in the first bone in a collapsed state, and wherein the second expandable section is configured to expand within the reverse countersink such that the at least one expandable feature couples to a bearing surface of the reverse countersink.

7. The bone implant of claim 6, wherein the second expandable section comprises a plurality of expandable arms.

8. The bone implant of claim 1, wherein the first expandable section comprises a material selected from the group consisting of: Nitinol, titanium, alloy, and stainless steel.

9. The bone implant of claim 1, wherein the first bone comprises a proximal phalanx and the second bone comprises a middle phalanx.

10. The bone implant of claim 1, wherein the elongate shaft extends a predetermined length such that when the first end is fully inserted into the first bone and the second end is fully inserted into the second bone there is substantially no gap between the first and second bones.

11. A surgical system, comprising:
    a surgical tool, comprising:
        a shaft sized and configured to be received within a canal formed in a bone, the shaft having a conical head with a pointed tip at a distal end of the shaft; and
        at least one expandable cutting edge formed integrally with the shaft, wherein the expandable cutting edge comprises a collapsed position configured for insertion into the canal with the expandable cutting edge extending away from the pointed tip, in a proximal direction toward a proximal end of the shaft and an expanded position configured to form a reverse countersink in the canal with the expandable cutting edge extending in a direction having a radial component and a component in the proximal direction, and wherein the expandable cutting edge is configured to be deployed to the expanded position after being inserted into the canal; and
    a surgical implant, comprising:
        a first end configured to couple to a first bone;
        a second end;
        a first expandable section comprising at least one expandable feature, wherein the first expandable section is sized and configured to be received within a reverse countersink formed in a second bone in a collapsed state, and wherein the first expandable section is configured to expand within the reverse countersink such that the at least one expandable feature couples to a bearing surface of the reverse countersink, wherein the at least one expandable feature comprises a plurality of expandable arms each having a connection end and a free end, the connection end coupled to a distal portion of the second end and the free end being proximally disposed relative to the connection end to couple to the bearing surface of the reverse countersink, wherein the free ends of the plurality of expandable arms define a first diameter when in a collapsed state and a second diameter when fully expanded, and further wherein the countersink defines a countersink diameter, the second diameter being equal to or greater than the countersink diameter; and
        an elongate shaft extending longitudinally between the first end and the second end, wherein a proximal portion of the second end is coupled to the elongate shaft.

12. The surgical system of claim 11, wherein the conical head is configured to contact an end of the canal and to space the expandable cutting edge a predetermined distance from the end of the canal.

13. The surgical system of claim 11, wherein the at least one expandable cutting edge is deployed by mechanical deflection.

14. The surgical tool system of claim 11, wherein the at least one expandable cutting edge comprises a hinge.

15. The surgical system of claim 11, wherein the at least one expandable cutting edge is configured to form the reverse countersink when the shaft is rotated.

16. A method for correcting hammertoe, comprising the steps of:
   forming a first canal in a first bone;
   forming a second canal in a second bone;
   inserting a surgical instrument into the second canal, wherein the surgical instrument comprises a shaft, a conical head with a pointed tip located at a distal end of the shaft, and an expandable cutting edge formed integrally with the shaft and deployable from a collapsed position with the expandable cutting edge extending away from the pointed tip, in a proximal direction toward a proximal end of the shaft, to an expanded position with the expandable cutting edge extending in a direction having a radial component and a component in the proximal direction; and
   rotating the surgical tool to form a reverse countersink in the second canal of the second bone
   inserting a first end of the implant into the first canal in the first bone;
   inserting a second end of an implant into the second canal in the second bone, the implant comprising an expandable section wherein the expandable section comprises at least one expandable feature, wherein the expandable section is inserted through the second canal to the reverse countersink in a collapsed position, wherein the at least one expandable feature expands within the reverse countersink such that the at least one expandable feature couples to a bearing surface of the reverse countersink, and wherein the at least one expandable feature comprises a plurality of expandable arms each having a connection end and a free end, the connection end coupled to a distal portion of the second end and the free end being proximally disposed relative to the connection end to couple to the bearing surface of the reverse countersink, wherein the free ends of the plurality of expandable arms define a first diameter when in a collapsed state and a second diameter when fully expanded, and further wherein the countersink defines a countersink diameter, the second diameter being equal to or greater than the countersink diameter.

17. The method of claim 16, wherein the canal exerts a force on the expandable section to maintain the expandable section in a collapsed state during insertion, and wherein the at least one expandable feature deploys when fully inserted into the reverse countersink.

18. The method of claim 16, wherein the first end of the implant comprises a threaded section, and wherein inserting the first end of the implant comprises rotating the threaded section into engagement with the first canal.

19. A method for correcting hammertoe, comprising the steps of:
   forming a first canal in a first bone;
   forming a second canal in a second bone;
   inserting a surgical instrument into the first canal, wherein the surgical instrument comprises a shaft, a conical head with a pointed tip located at a distal end of the shaft, and an expandable cutting edge formed integrally with the shaft and deployable from a collapsed position with the expandable cutting edge extending away from the pointed tip, in a proximal direction toward a proximal end of the shaft, to an expanded position with the expandable cutting edge extending in a direction having a radial component and a component in the proximal direction;
   rotating the surgical tool to form a reverse countersink in the first canal of the first bone;
   inserting the surgical instrument into the second canal;
   rotating the surgical tool to form a reverse countersink in the second canal of the second bone; and
   inserting a first end of an implant into the first canal in the first bone, the implant comprising a first expandable section having at least one expandable feature, wherein the first expandable section is inserted through the first canal to the reverse countersink in a collapsed position, and wherein the at least one expandable feature expands within the reverse countersink such that the at least one expandable feature couples to a bearing surface of the reverse countersink, and wherein the at least one expandable feature comprises a plurality of expandable arms each having a connection end and a free end, the connection end coupled to a proximal portion of the first end and the free end being distally disposed relative to the connection end to couple to the bearing surface of the reverse countersink, wherein the free ends of the plurality of expandable arms define a first diameter when in a collapsed state and a second diameter when fully expanded, and further wherein the countersink defines a countersink diameter, the second diameter being equal to or greater than the countersink diameter.

20. The method of claim 19, wherein the first canal exerts a force on the first expandable section to maintain the first expandable section in a collapsed state during insertion, and wherein the at least one expandable feature deploys when fully inserted into the reverse countersink.

21. The method of claim 19, further comprising inserting a second end of the implant into the second canal in the second bone, the implant comprising a second expandable section having at least one expandable feature, wherein the second expandable section is inserted through the second canal to the reverse countersink in a collapsed position, and wherein the at least one expandable feature expands within the reverse countersink such that the at least one expandable feature couples to a bearing surface of the reverse countersink.

22. The method of claim 21, wherein the second canal exerts a force on the second expandable section to maintain the second expandable section in a collapsed state during insertion, and wherein the at least one expandable feature deploys when fully inserted into the reverse countersink.

* * * * *